(12) United States Patent
Alsberg et al.

(10) Patent No.: US 11,471,565 B2
(45) Date of Patent: *Oct. 18, 2022

(54) ENGINEERED TISSUE CONSTRUCTS

(71) Applicants: CASE WESTERN RESERVE UNIVERSITY, Cleveland, OH (US); WORCESTER POLYTECHNIC INSTITUTE, Worcester, MA (US)

(72) Inventors: Eben Alsberg, Cleveland, OH (US); Anna D. Dikina, Cleveland, OH (US); Marsha W. Rolle, Worcester, MA (US)

(73) Assignees: CASE WESTERN RESERVE UNIVERSITY, Cleveland, OH (US); WORCESTER POLYTECHNIC INSTITUTE, Worcester, MA (US)

( * ) Notice: Subject to any disclaimer, the term of this patent is extended or adjusted under 35 U.S.C. 154(b) by 24 days.

This patent is subject to a terminal disclaimer.

(21) Appl. No.: 15/258,666

(22) PCT Filed: Mar. 9, 2015

(86) PCT No.: PCT/US2015/019541
§ 371 (c)(1),
(2) Date: Sep. 7, 2016

(87) PCT Pub. No.: WO2015/134999
PCT Pub. Date: Sep. 11, 2015

(65) Prior Publication Data
US 2017/0183629 A1 Jun. 29, 2017

Related U.S. Application Data

(60) Provisional application No. 61/970,653, filed on Mar. 26, 2014, provisional application No. 61/949,552, filed on Mar. 7, 2014.

(51) Int. Cl.
A61L 27/38 (2006.01)
A61L 27/54 (2006.01)
C12N 5/00 (2006.01)

(52) U.S. Cl.
CPC ....... *A61L 27/3882* (2013.01); *A61L 27/3804* (2013.01); *A61L 27/54* (2013.01);
(Continued)

(58) Field of Classification Search
None
See application file for complete search history.

(56) References Cited

U.S. PATENT DOCUMENTS 6,886,568 B2 * 5/2005 Frondoza ............ A61K 9/0019
128/898
2007/0042490 A1 2/2007 Welter et al.

OTHER PUBLICATIONS

Schrobback et al., J. Orthop. Res. 29: 539-546 (2011).*
(Continued)

*Primary Examiner* — Erin M. Bowers
(74) *Attorney, Agent, or Firm* — Tarolli, Sundheim, Covell & Tummino LLP

(57) ABSTRACT

A modular engineered tissue construct includes a plurality of fused self-assembled, scaffold-free, high-density cell aggregates. At least one cell aggregate includes a plurality of cells and a plurality of biocompatible and biodegradable nanoparticles and/or microparticles that are incorporated within the cell aggregates. The nanoparticles and/or microparticles acting as a bulking agent within the cell aggregate to increase the cell aggregate size and/or thickness and improve the mechanical properties of the cell aggregate as well as to deliver bioactive agents.

12 Claims, 17 Drawing Sheets
Specification includes a Sequence Listing.

(52) U.S. Cl.
CPC ...... *C12N 5/0075* (2013.01); *A61L 2300/414* (2013.01); *A61L 2300/602* (2013.01); *A61L 2300/62* (2013.01); *A61L 2400/12* (2013.01); *A61L 2430/22* (2013.01); *C12N 2513/00* (2013.01); *C12N 2531/00* (2013.01)

(56) References Cited

OTHER PUBLICATIONS

Steiner et al., J. Orthop. Res. 30: 1682-1689 (2012).*
European Office action for Application No. 15758207.3-1120, dated Jan. 10, 2019.
Anna D. Dikina et al: "Engineered cartilaginous tubes for tracheal tissue replacement via self-assembly and fusion of human mesenchymal stem cell constructs", Biomaterials., vol. 52, Jun. 1, 2015 (Jun. 1, 2015), pp. 452-462.
European Office action for Application No. 15758207.3-1120, dated Jul. 26, 2019.
Loran D. Solorio et al: "High-Density Cell Systems Incorporating Polymer Microspheres as Microenvironmental Regulators in Engineered Cartilage Tissues", Tissue Engineering Part Breviews, vol. 19, No. 3, Jun. 1, 2013 (Jun. 1, 2013), pp. 209-220.
Singh M et al: "Microsphere-based scaffolds for cartilage tissue engineering: Using subcritical C0"2 as a sintering agent", Acta Biomaterialia, vol. 6, No. 1, Jan. 1, 2010 (Jan. 1, 2010), pp. 137-143.
Loran D. Solorio et al: "Spatiotemporal Regulation of Chondrogenic Differentiation with Controlled Delivery of Transforming Growth Factor-[beta]1 from Gelatin Microspheres in Mesenchymal Stem Cell Aggregates", Stem Cells Translational Medicine : SCTM, vol. 1, No. 8, Aug. 1, 2012 (Aug. 1, 2012), pp. 632-639.
Olufunmilayo Adebayo et al: "Self-assembled smooth muscle cell tissue rings exhibit greater tensile strength than cell-seeded fibrin or collagen gel rings", Journal of Biomedical Materials Research. Part A, vol. 101 A, No. 2, Aug. 3, 2012 (Aug. 3, 2012), pp. 428-437.

* cited by examiner

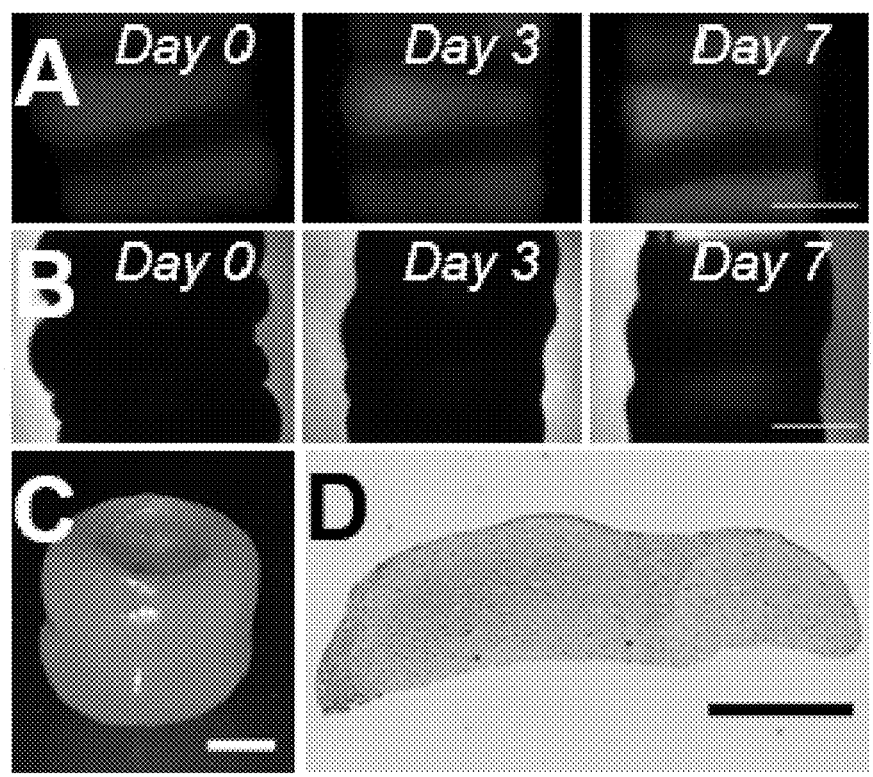
Figs. 3A-D
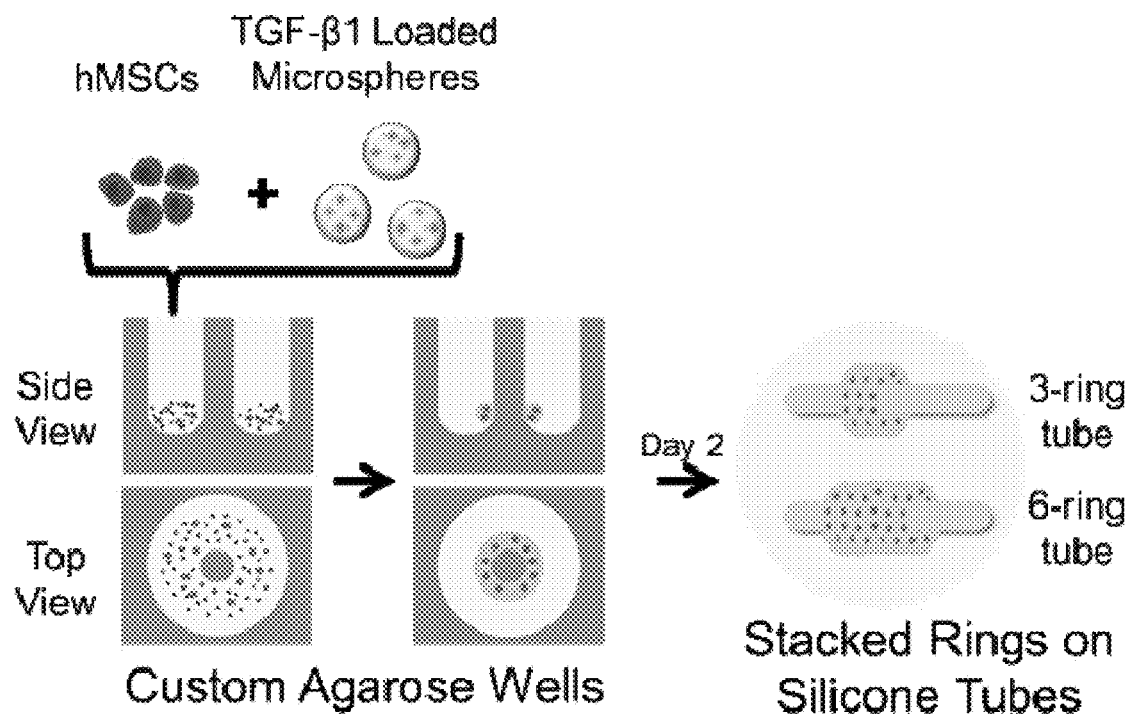
Fig. 4

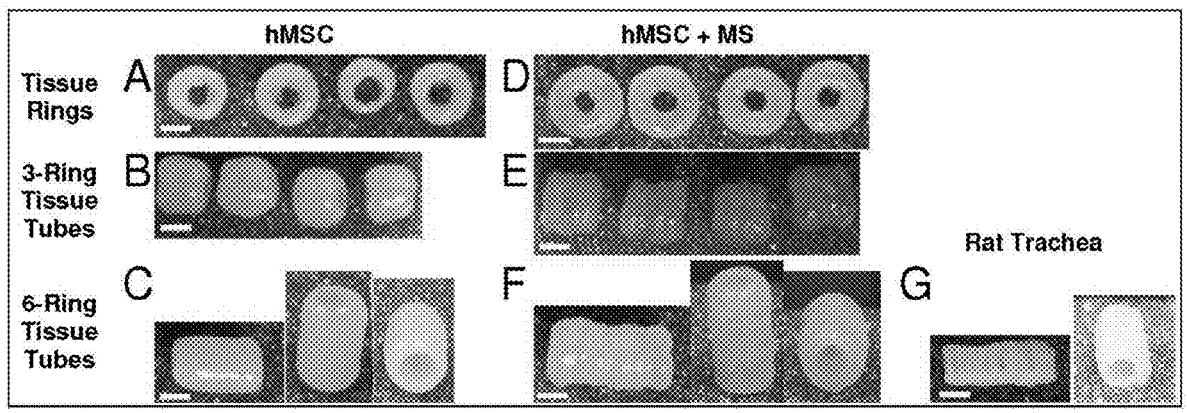
Figs. 7A-G
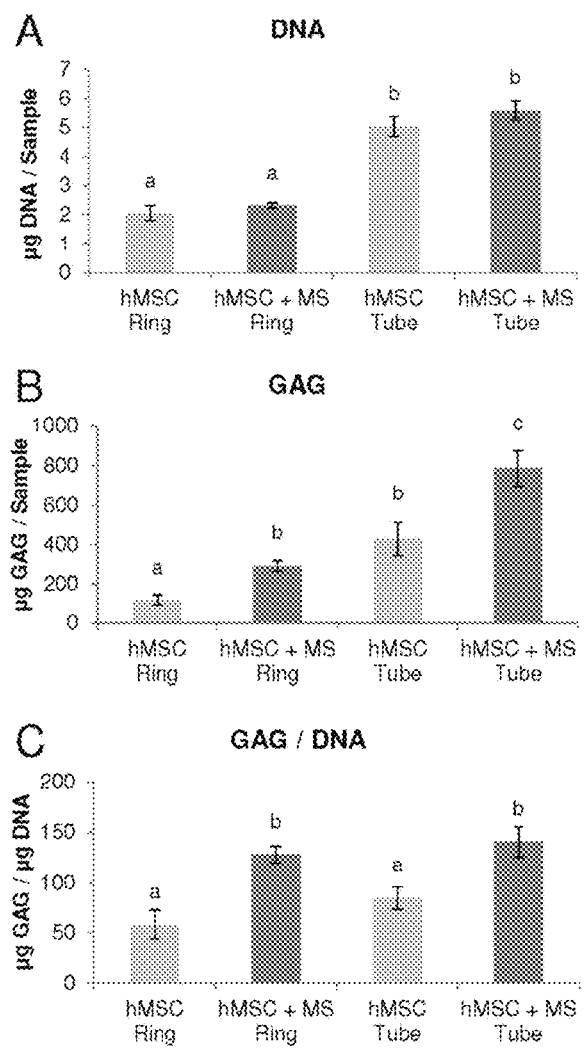
Figs. 8A-C

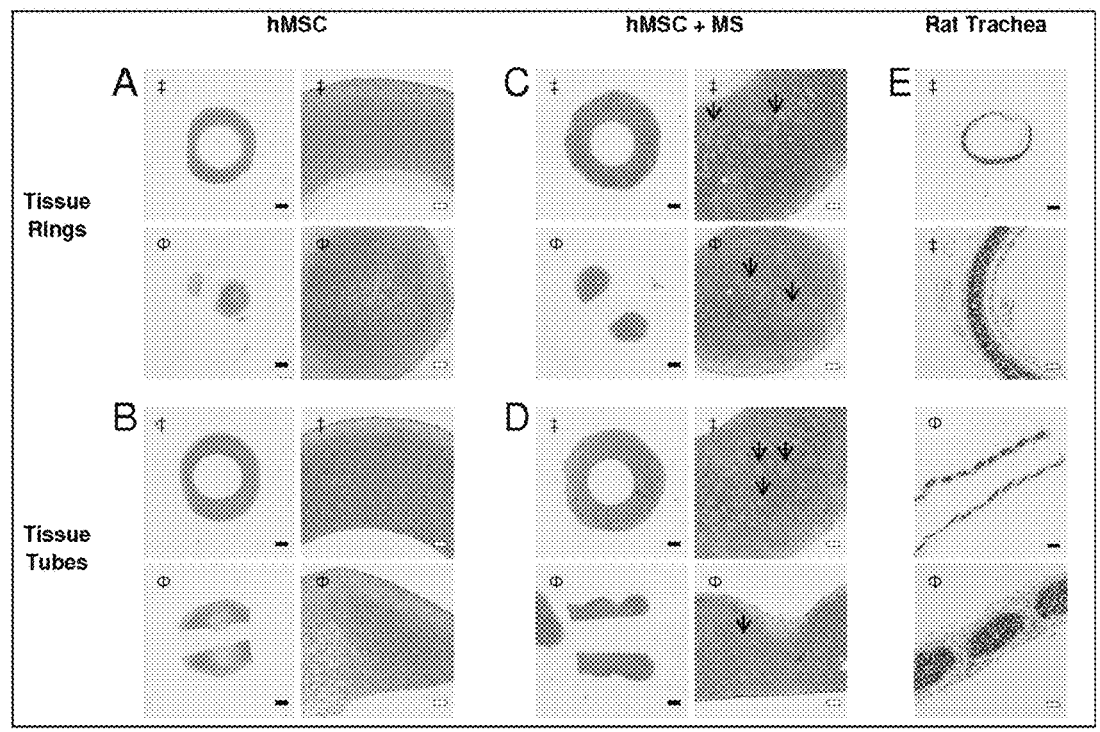
Figs. 9A-E
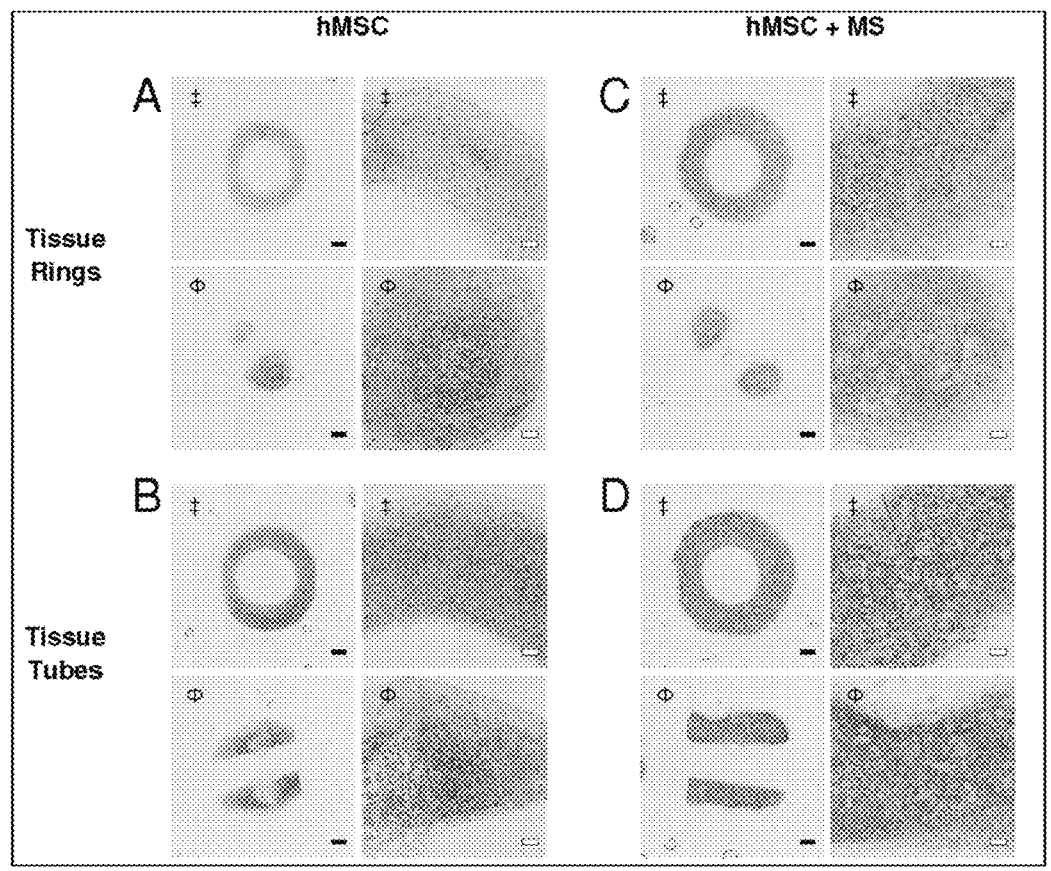
Figs. 10A-D

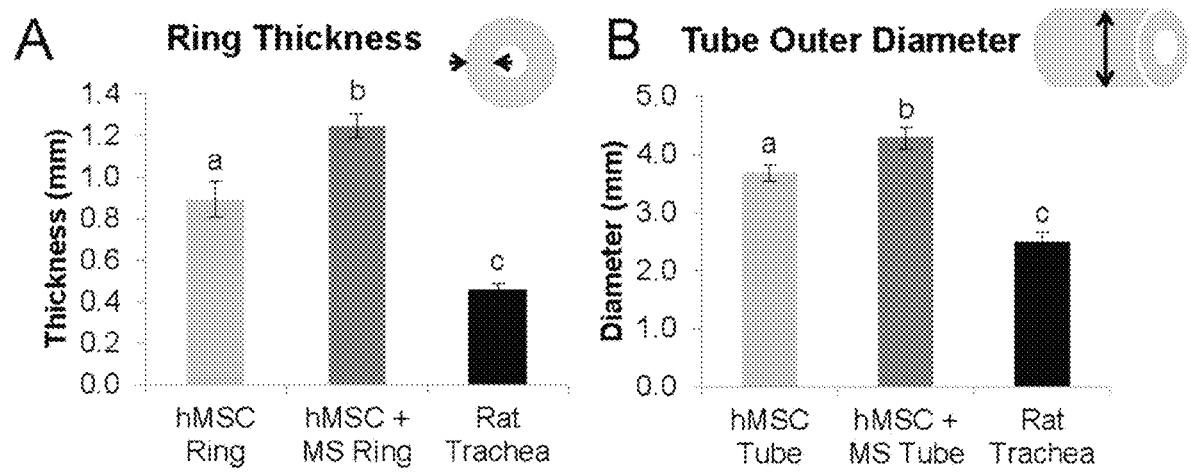
Figs. 11A-B
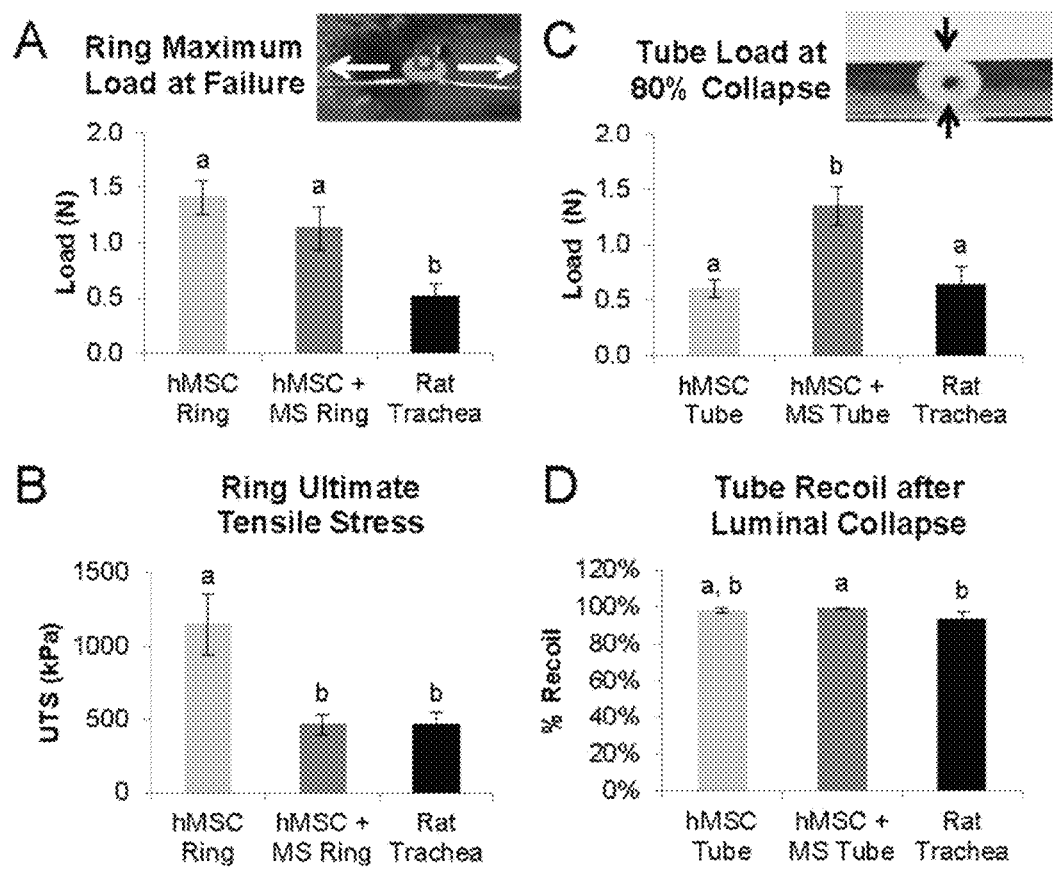
Figs. 12A-D

Figs. 15A-F

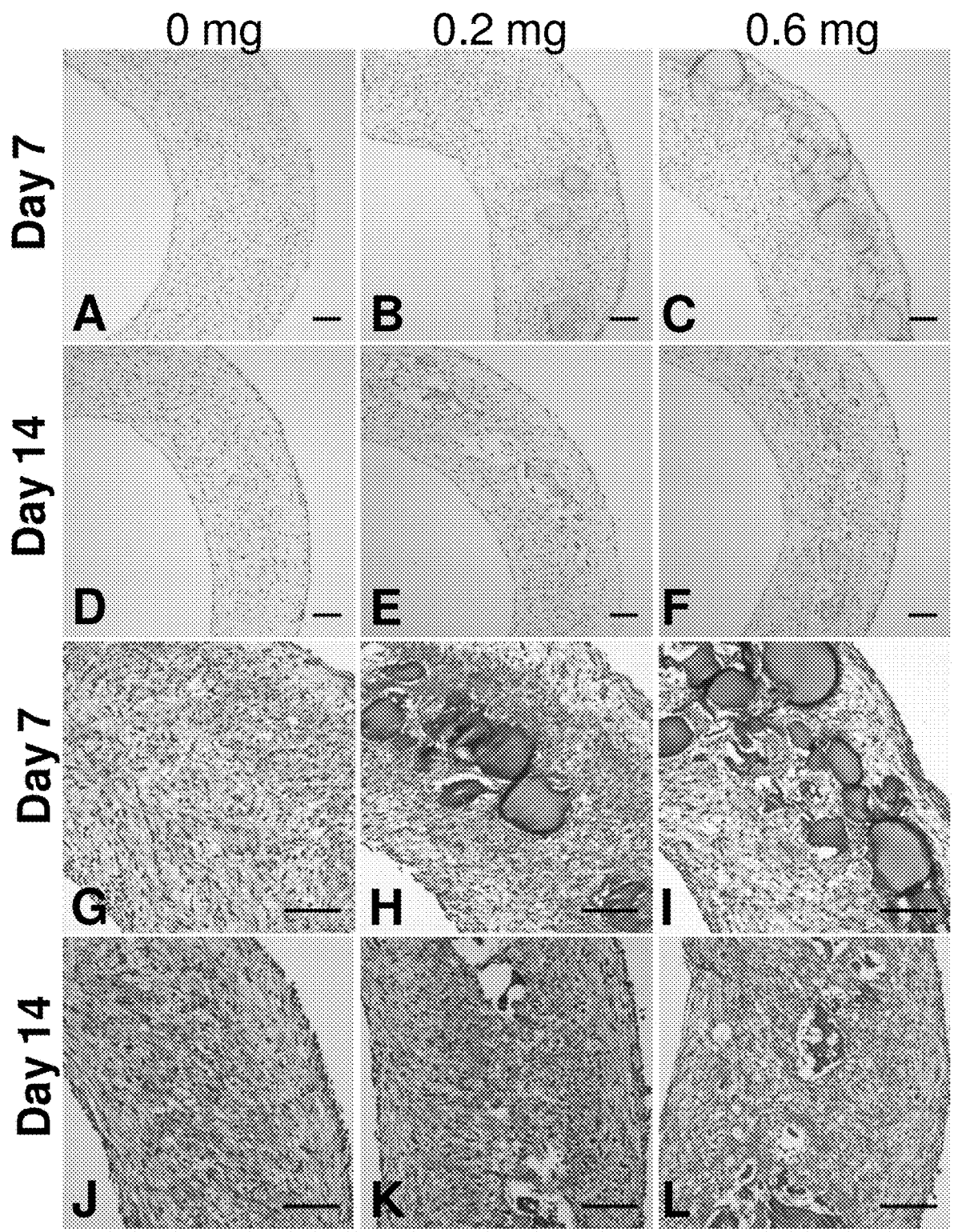
Figs. 18A-L

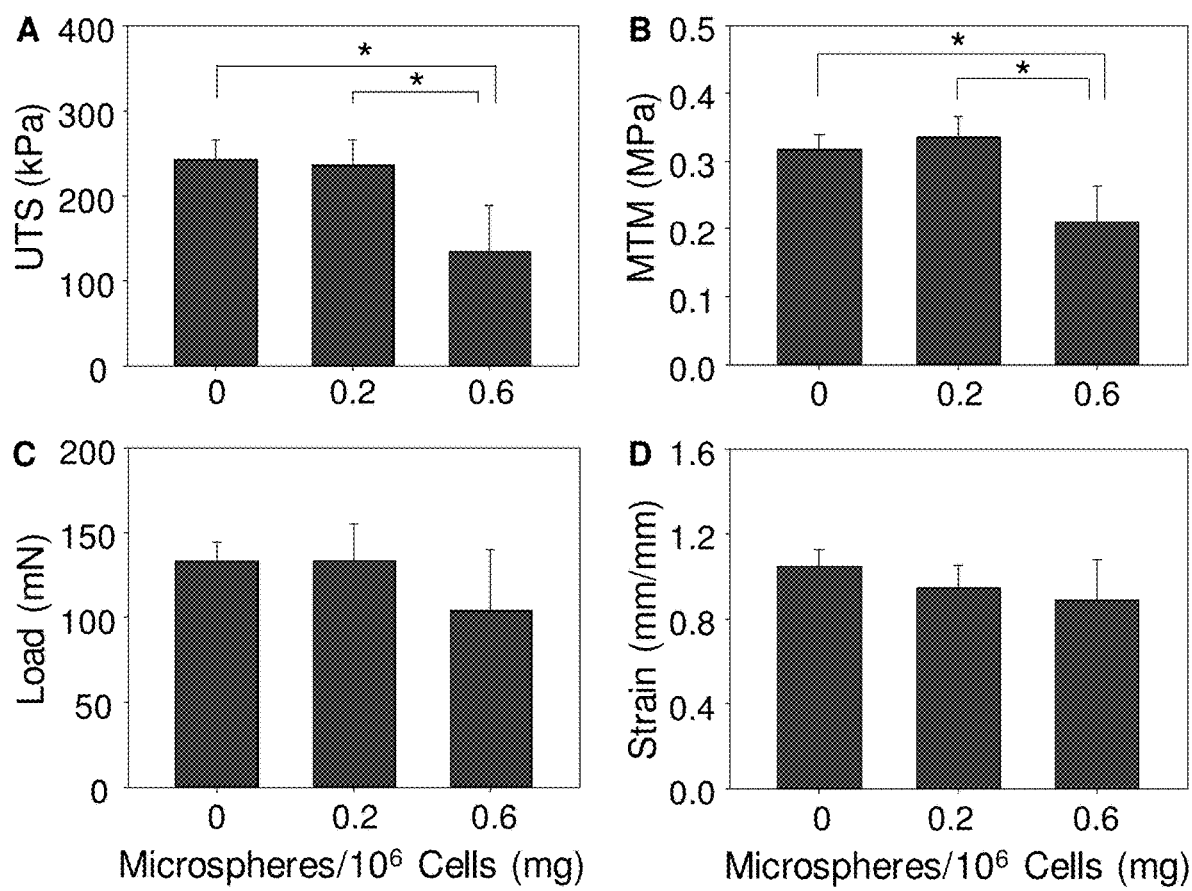
Figs. 19A-D

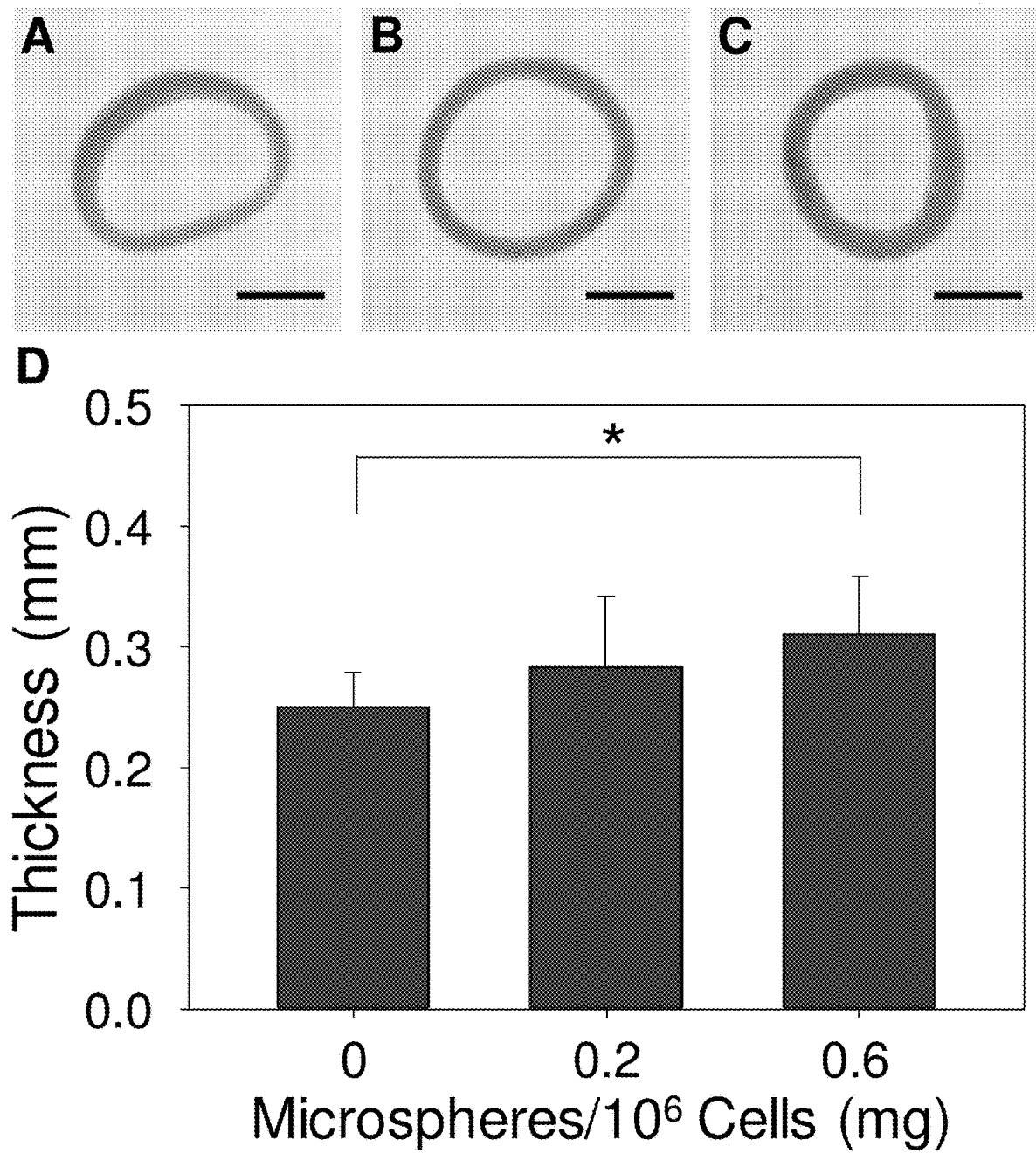
Figs. 20A-D

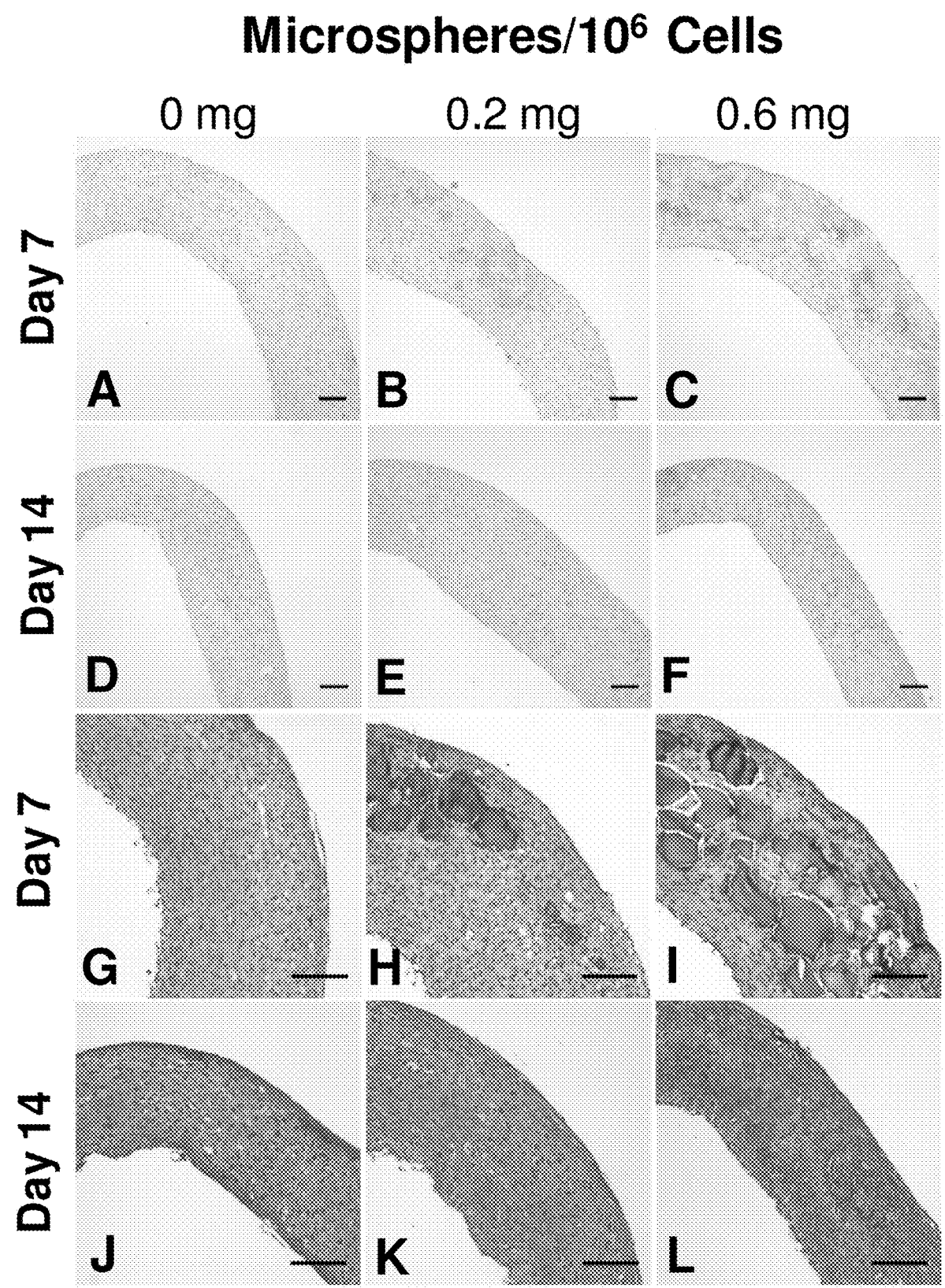
Figs. 21A-L

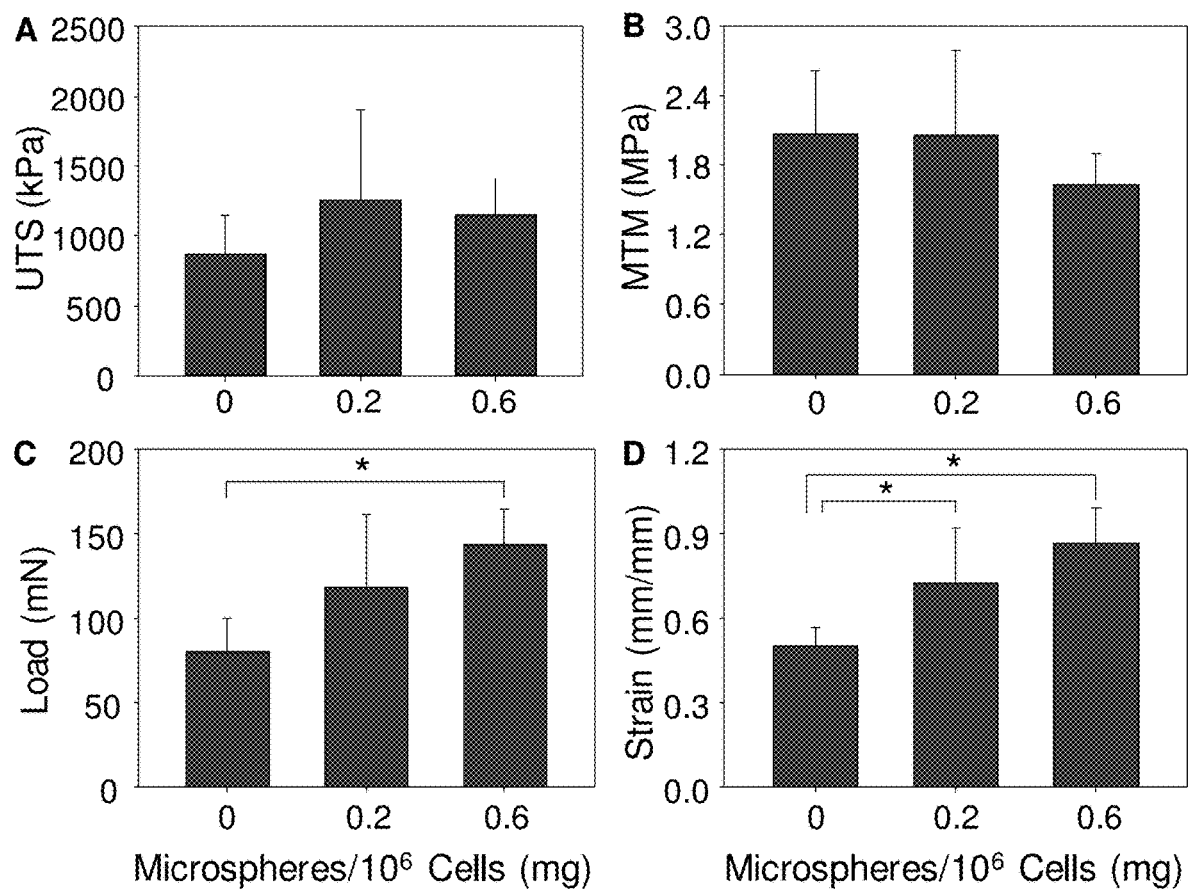
Figs. 22A-D

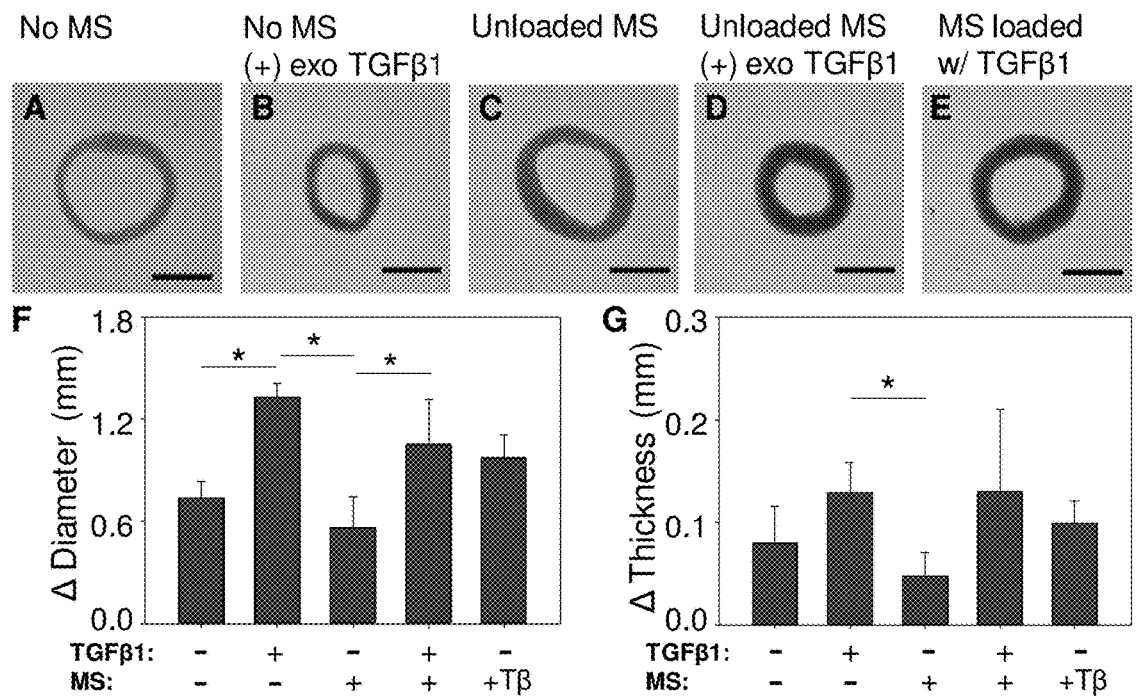
Figs. 23A-G
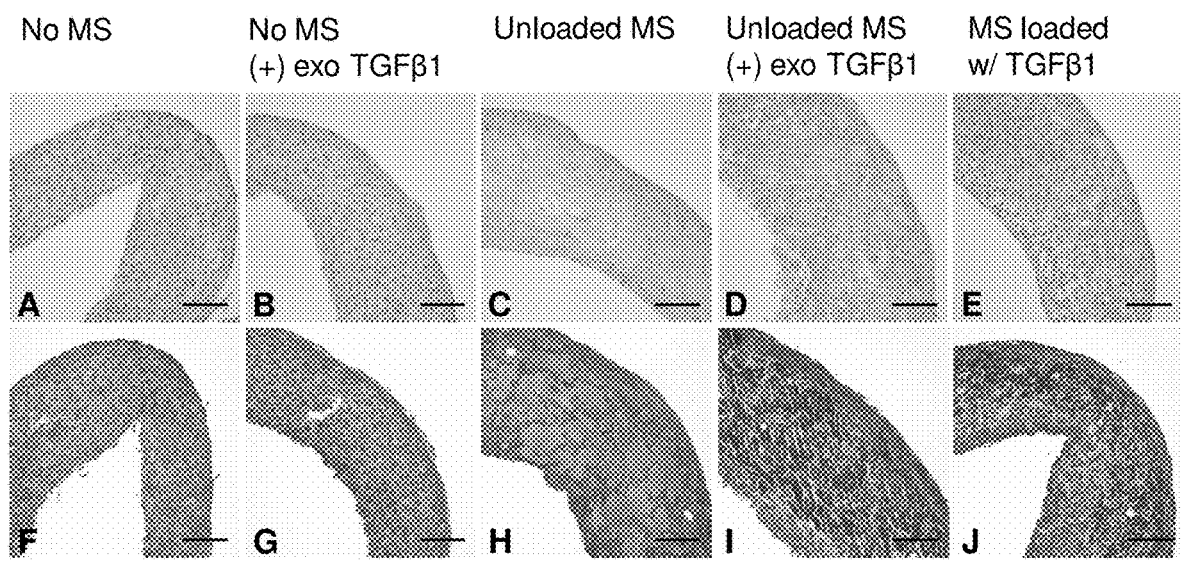
Figs. 24A-J

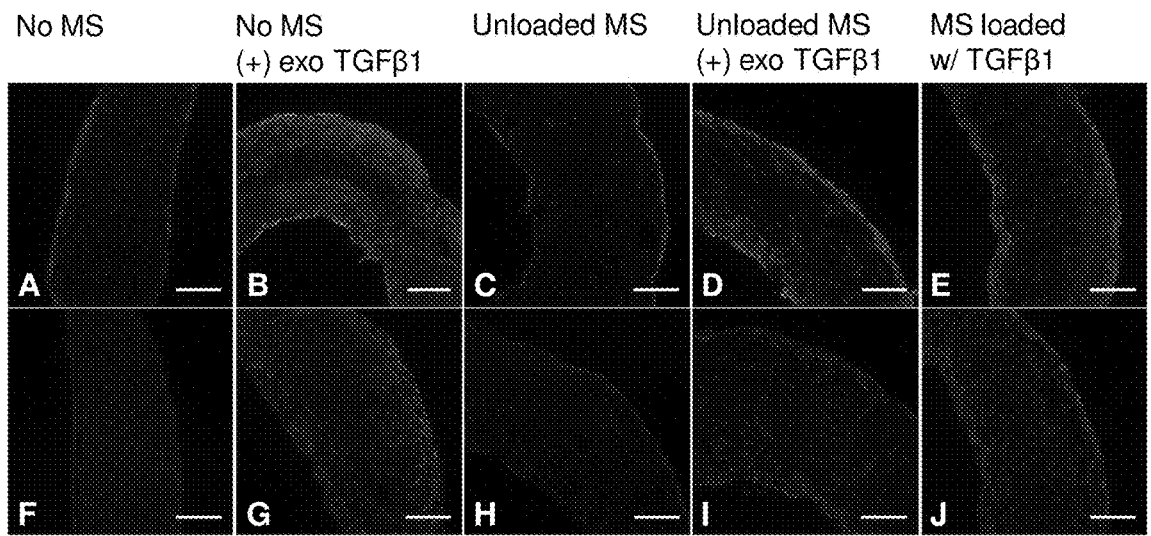
Figs. 25A-J
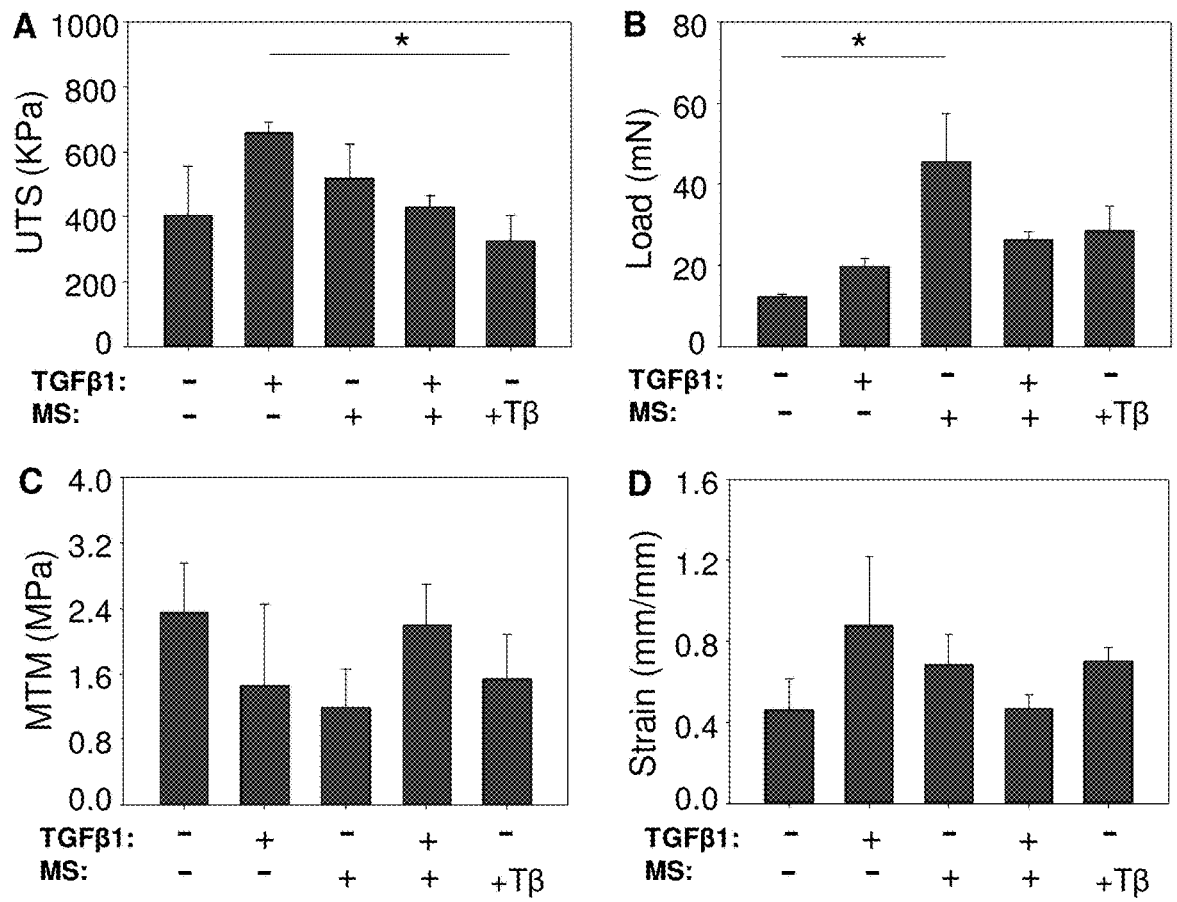
Figs. 26A-D

ENGINEERED TISSUE CONSTRUCTS

RELATED APPLICATION

This application is a Continuation-in-Part of PCT/US2015/019541, filed Mar. 9, 2015, which claims priority from U.S. Provisional Application No. 61/949,552, filed Mar. 7, 2014. This application also claims priority to U.S. Provisional Application Ser. No. 62/384,400, filed Sep. 7, 2016, the subject matter of which are incorporated herein by reference in their entirety.

GOVERNMENT FUNDING

This invention was made with government support under Grant Nos. R01AR063194, T32AR007505, awarded by The National Institutes of Health, and DGE1144804 awarded by the National Science Foundation. The United States government has certain rights to the invention.

TECHNICAL FIELD

The present application relates to engineered tissue constructs, and systems and methods of forming the engineered tissue constructs.

BACKGROUND

Narrowing or collapse of the trachea is a life threatening condition because stenosis or malacia can prohibit sufficient air transport to the lungs. The most common cause of adult tracheal stenosis is trauma due to prolonged intubation or tracheostomy, but other causes include perichondritis, chondritis, tumor, burns and external trauma. Typically, if the affected portion is less than half the entire length of the trachea in adults or one third in children, the diseased region can be resected and the healthy ends anastomosed during tracheal reconstruction surgery. While short, resectable stenoses are far more common, there are limited treatments available for lengthy tracheal occlusions. Short-term solutions for patients with long segment stenosis include stents, T-tubes, laser surgery and airway dilation. However, a major drawback to these is the need for repetitive treatment: periodic stent and tube replacement due to granuloma formation or additional laser surgery and dilation due to scarring and restenosis. As a result, biomaterial and tissue engineering approaches have been pursued to develop tracheal substitutes. A functional tracheal replacement must first and foremost maintain airway patency during normal breathing. Normally, healthy tracheal cartilage supports the open windpipe. Acellular tracheal prostheses are made of rigid materials and tissue engineered cell-laden technologies are typically cartilaginous structures that are designed to mimic the trachea. A variety of tracheal replacement strategies have been explored, including cell-free artificial prostheses, autografts, native or decellularized allografts which are often seeded with the recipient's cells, and autologous de novo tissue engineered constructs. Despite the broad range of approaches, each has shortcomings. Acellular tracheal prostheses often result in tissue granulation, implant migration, progressive scar tissue formation and restenosis. Autografts and allografts have limited availability, poor mechanical properties, and undergo remodeling upon implantation, often leading to collapse, scarring, and airway occlusion. Allogeneic donor tissue also carries a risk of disease transmission and immunogenicity; recipients of native tissues must be immunosuppressed and extra care must be taken to remove antigens from decellularized tissues. Tissue engineered constructs comprised of autologous cells in scaffolds circumvent immune response issues, but the structural, physical and biochemical properties of the scaffold must be carefully designed to guide cell behavior and neotissue formation. It is also challenging to tune the scaffold degradation rate to match that of cell proliferation and new extracellular matrix (ECM) production, and biomaterial degradation byproducts may hinder tissue healing.

SUMMARY

Embodiments described herein relate to engineered tissue constructs with defined shapes, such as engineered tissue rings, systems and methods of forming modular engineered tissue constructs and to the use of modular engineered tissue constructs in modular tissue assembly systems for tissue repair and bio-artificial tissue engineering applications, such as engineered trachea constructs. The engineered tissue constructs can include self-assembled, scaffold-free, cell aggregates that are formed by culturing a plurality of cells and nanoparticles and/or microparticles in wells with defined shapes, e.g., rings, disks, or blocks, of a cell culture apparatus or bioreactor. In some embodiments, the self-assembled, cell aggregate can include a population or plurality of cells and plurality of nanoparticles and/or microparticles that are incorporated within the cell aggregate. The nanoparticles and/or microparticles can act as a bulking agent within the cell aggregate to increase the cell aggregate size and/or thickness. Incorporation of the nanoparticles and/or microparticles in the cell aggregate can also improve the mechanical properties of the cell aggregate formed from the cells and nanoparticles and/or microparticles allowing the cell aggregate to be readily manipulated and formed into engineered tissue constructs.

In some embodiments, the nanoparticles and/or microparticles can include at least one bioactive agent that is differentially and/or controllably released by the nanoparticles and/or microparticles. In some embodiments, the bioactive agent can be physically associated with the nanoparticles and/or microparticles and spatially and/or temporally released with a defined release profile from the nanoparticles and/or microparticles.

The engineered tissue constructs can be used in a tissue assembly system to engineer human tissue containing, for example, engineered cartilaginous, vascular, prevascular, muscular, and bone segments. The tissue assembly system can permit fusion of engineered tissue constructs having different properties together to generate modular constructs with multiple types of tissues in a spatially-controlled pattern. Culture of heterogeneous engineered tissue constructs in a hollow organ bioreactor can permit further modification of the constructs, including, for example, epithelialization, of a surface of the construct.

BRIEF DESCRIPTION OF THE DRAWINGS

FIG. 3 illustrates images of heterogenous cartilage tube with cartilaginous and non-cartilaginous portions. Chondrogenesis was induced in hMSC rings for (A-B) 5 days or (C-D) 12 days. SMC rings were cultured for (A-B) 10 days or (C-D) 5 days. Alternating hMSC and SMC rings were fused into (A-B) 10-ring tubes over 7 days or (C-D) 4-ring tubes over 8 days. (A) Fluorescence (hMSC labeled with red cell tracker dye) and (B) brightfield images of hMSC-SMC tubes. (C) hMSC-SMC tube after 8 days of fusing. (D) Cross-section of hMSC-SMC tube stained with Safranin O/Fast Green for GAG (lumen is on bottom). Scale bars: white=1 mm, black=500 μm.

FIG. 4 is a schematic of tissue ring and tube assembly processes. A suspension of MSCs with growth factor loaded microspheres ("hMSC+MS") was seeded in custom agarose wells and cultured in basal pellet media. Cell only tissues ("hMSC"), which did not contain microspheres, were seeded and cultured in basal pellet media supplemented with TGF-β1. On day 2 of culture, rings (tan) were removed from the culture wells using tweezers and were stacked on silicone tubes (gray) to form 3- and 6-ring tubes.

FIG. 7 illustrates gross macroscopic pictures of (A-C) hMSC-only cartilage rings and tubes, (D-F) microsphere-containing rings and tubes, and (G) native rat trachea. (A, B, D, E) Rings and 3-ring tubes are shown in replicates. (C, F, G). A representative hMSC or hMSC+MS 6-ring tube and a rat trachea are presented from multiple perspectives. MS=Microspheres. Scale bar is 2 mm.

FIG. 8 illustrates (A) DNA content, (B) GAG content, and (C) GAG normalized to DNA in harvested rings and 3-ring cartilage tubes. MS=Microspheres. Groups that do not share the same letter are significantly different ($p<0.01$).

FIG. 9 illustrates photomicrographs of Safranin 0/Fast Green stained tissue engineered (A, C) cartilage rings and (B, D) cartilage tubes composed of (A, B) hMSCs-only and (C, D) hMSCs+MS, and (E) rat trachea in axial and vertical planes. Remnant gelatin microspheres (black arrows) are visible in hMSC+MS tissues. MS=Microspheres; F=axial plane; z=vertical plane; black scale bars=500 mm; white scale bars=100 mm.

FIG. 10 illustrates photomicrographs of Collagen Type II/Fast Green stained tissue engineered (A, C) cartilage rings and (B, D) cartilage tubes composed of (A, B) hMSCs-only (A, B) and (C, D) hMSCs+MS in axial and vertical planes. Type II collagen rich tissues are red. MS=Microspheres; F=axial plane; z=vertical plane; black scale bars=500 mm; white scale bars=100 mm.

FIG. 11 illustrates ring thicknesses (A) and tube outer diameters (B) measured in cartilage tissue engineered rings and tubes, and rat tracheas. MS=Microspheres. Groups that do not share a letter are significantly different ($p<0.05$).

FIG. 12 illustrates mechanical analysis of tissue engineered cartilage rings and tubes, and rat tracheas. (A) Ring maximum load at failure and (B) ultimate tensile stress during uniaxial testing (A, inset); (C) tube load at 80% collapse and (D) % recoil after luminal collapse (C, inset). MS=Microspheres. Groups that do not share the same letter are significantly different ($p<0.05$).

FIG. 18 illustrates images showing gelatin microsphere incorporation and degradation within vascular tissue rings. Tissue rings were seeded with 0, 0.2, or 0.6 mg microspheres per million cells, collected at 7 or 14 days, and stained with Hematoxylin and Eosin (A-F) and Picrosirius Red/Fast Green stain. Scale=100 μm.

FIG. 19 illustrates graphs showing mechanical properties of vascular tissue rings loaded with gelatin microspheres. Self-assembled cell rings were cultured for 14 days in growth medium and pulled to failure. Mean values for ultimate tensile strength (UTS; A), maximum tangent modulus (MTM; B), failure load (C) and failure strain (D) were calculated from stress-strain curves for each ring sample group. n=6, *$p<0.05$.

FIG. 20 illustrates an image and graph showing microspheres increased ring thickness in tissues cultured in smooth muscle differentiation medium. Rings were seeded with 0 (A), 0.2 (B), or 0.6 mg (C) of microspheres per million cells and cultured to 14 days. Rings were seeded in growth medium and switched to differentiation medium on day 1. (D) Average wall thicknesses of 14-day-old tissue rings with 0, 0.2, or 0.6 mg microspheres per million cells. Scale=1 mm; n=8 for 0 mg; n=9 for 0.2 and 0.6 mg/million cells; *$p<0.05$.

FIG. 21 illustrates images showing microsphere incorporation within tissue rings cultured in smooth muscle differentiation medium. Tissue rings were seeded in growth medium with 0, 0.2, or 0.6 mg microspheres per million cells, and switched to differentiation medium at day 1. Tissue rings were collected at 7 or 14 days, and stained with Hematoxylin and Eosin (A-F) and Picrosirius Red/Fast Green stain. Scale=100 μm.

FIG. 22 illustrates graphs showing the mechanical properties of tissue rings cultured in differentiation medium with microsphere incorporation. Self-assembled cell rings were seeded in growth medium, switched to differentiation medium on day 1, and cultured for 13 days in differentiation medium and harvested for mechanical tests (14 days total culture). Mean values for ultimate tensile strength (UTS; A), maximum tangent modulus (MTM; B), failure load (C) and failure strain (D) were calculated from stress-strain curves for each ring sample group. n=6, *p<0.05.

FIG. 23 illustrates images and a graph showing exogenous or microsphere-mediated TGF-β1 delivery to self-assembled tissue rings. Rings were seeded in growth medium, and switched to differentiation medium at day 1. (A) Untreated control rings with no microspheres (n=6). (B) Tissue rings treated with 10 ng/ml soluble TGF-β1 (n=8). (C,D) Tissue rings with unloaded gelatin microspheres (0.6 mg/million cells; n=6) untreated (C) or treated (D) with 10 ng/ml exogenous TGF-β1 (n=8). (E) Tissue rings with microspheres pre-loaded with TGF-β1 (400 ng TGF-β1/mg microspheres), but no exogenous TGF-β1 in the medium (n=7). Tissue rings contracted after they were removed from agarose posts, resulting in a greater decrease in diameter (F) and greater thickness (G) in rings exposed to TGF-β1. Scale=1 mm, *p<0.05.

FIG. 24 illustrates images showing hematoxylin and eosin stain (A-E) at 14 days shows microsphere degradation primarily in the groups with added TGF-β1. Collagen deposition in TGF-β1 groups is primarily seen around ring edges. (A,F) Control (untreated) rings. (B,G) Rings cultured with exogenous 10 ng/ml TGF-β1 added to the medium. Rings with unloaded microspheres (0.6 mg per million cells) untreated (C,H) or treated with 10 ng/ml exogenous TGF-β1 (D,I). Rings with TGF-β1 loaded microspheres (0.6 mg microspheres per million cells) and no exogenous TGF-β1 treatment (E, J). Scale=100 µm.

FIG. 25 illustrates images showing contractile protein expression in tissue rings treated with TGF-β1. Rings were grown with either no microspheres or exogenous TGF-β1 (A,F), no microspheres but treated with 10 ng/ml exogenous TGF-β1 (B,G), with microspheres and no exogenous TGF-β1 (C,H), with unloaded microspheres and exogenous TGF-β1 (D,I) or with TGF-β1 loaded microspheres and no exogenous TGF-β1 in the medium (E,J). Rings were stained for either smooth muscle alpha actin (A-E) or calponin (F-J). Nuclei are shown in blue (Hoechst). Scale=100 µm.

FIG. 26 illustrates graphs showing the mechanical properties of tissue rings treated with TGF-β1 after 14 days in culture. Rings were cultured in differentiation medium with no microspheres or exogenous TGF-β1, no microspheres with 10 ng/ml exogenous TGF-β1, unloaded microspheres with no exogenous TGF-β1, unloaded microspheres with 10 ng/ml exogenous TGF-β1, or loaded microspheres (400 ng TGF-β1/mg microspheres) and no exogenous TGF-β1. Rings in the group with no microspheres and exogenous TGF-β1 had significantly higher ultimate tensile stresses than the loaded microsphere group (A), and the unloaded microspheres without TGF-β1 group had significantly higher failure loads than rings without microspheres or TGF-β1 (B). There were no significant differences in MTM (C) or failure strain (D). *p<0.05.

DETAILED DESCRIPTION

Figure 1:
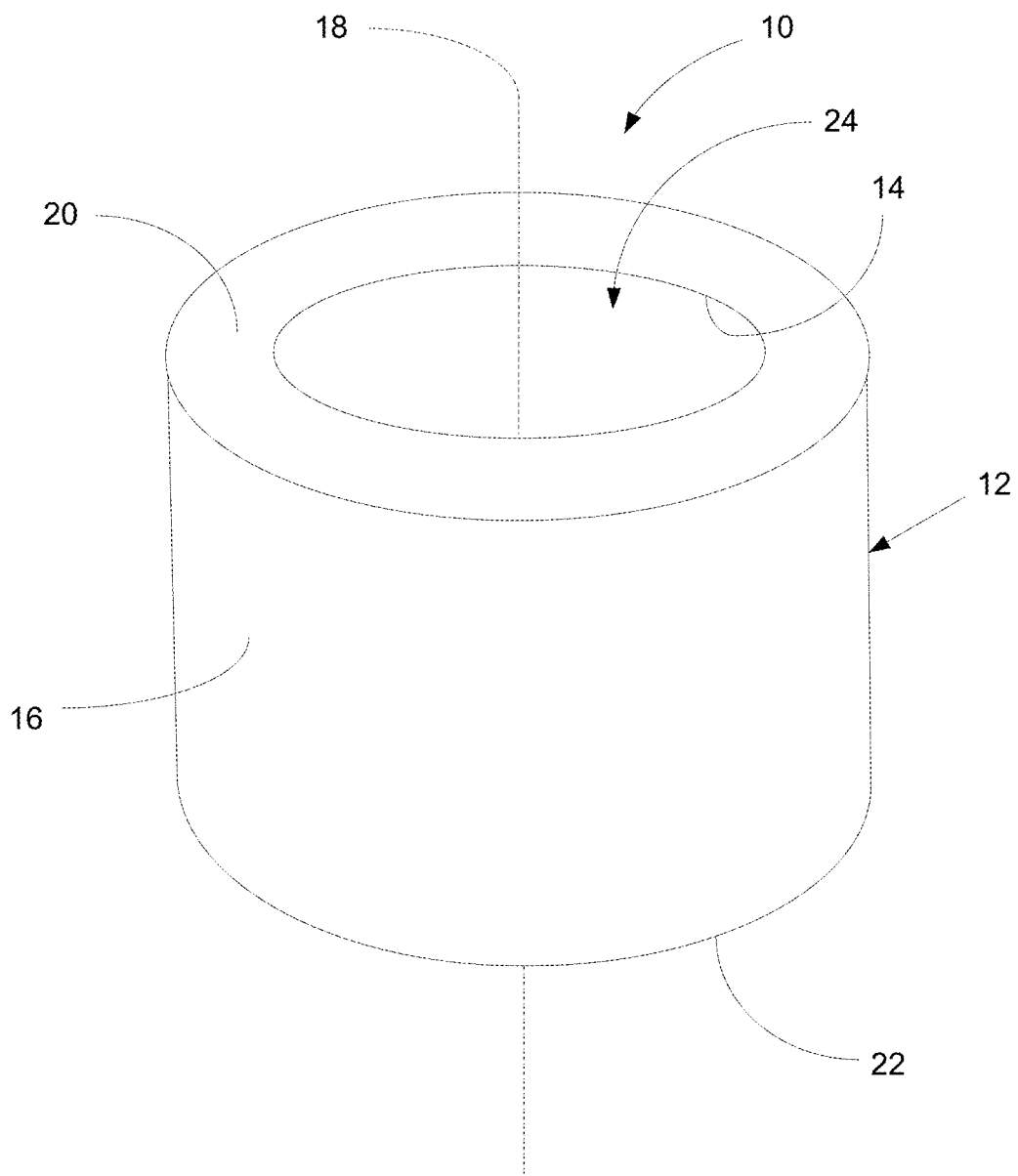
FIG. 1 is a schematic illustration of a method of forming an engineered tissue construct in accordance with an embodiment.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Ed., Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

As used herein, the term "autologous" refers to cells or tissues that are obtained from a donor and then re-implanted into the same donor.

As used herein, the term "allogeneic" refers to cells or tissues that are obtained from a donor of one species and then used in a recipient of the same species.

In the context of the present invention, the term "bioactive agent" can refer to any agent capable of promoting tissue formation, destruction, and/or targeting a specific disease state. Examples of bioactive agents can include, but are not limited to, chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin-like growth factor (e.g., IGF-I, IGF-II) and transforming growth factors (e.g., TGF-β I-III), parathyroid hormone, parathyroid hormone related peptide, bone morphogenic proteins (e.g., BMP-2, BMP-4, BMP-6, BMP-7, BMP-12, BMP-13, BMP-14), transcription factors, such as sonic hedgehog, growth differentiation factors (e.g., GDF5, GDF6, GDF8), recombinant human growth factors (e.g., MP52 and the MP-52 variant rhGDF-5), cartilage-derived morphogenic proteins (CDMP-1, CDMP-2, CDMP-3), small molecules that affect the upregulation of specific growth factors, tenascin-C, hyaluronic acid, chondroitin sulfate, fibronectin, decorin, thromboelastin, thrombin-derived peptides, heparin-binding domains, heparin, heparan sulfate, polynucleotides, DNA fragments, DNA plasmids, MMPs, TIMPs, interfering RNA molecules, such as siRNAs, oligonucleotides, proteoglycans, glycoproteins, glycosaminoglycans, and DNA encoding for shRNA.

As used herein, the terms "biodegradable" and "bioresorbable" may be used interchangeably and refer to the ability of a material (e.g., a natural polymer or macromer) to be fully resorbed in vivo. "Full" can mean that no significant extracellular fragments remain. The resorption process can involve elimination of the original implant material(s) through the action of body fluids, enzymes, cells, and the like.

As used herein, the term "carrier material" can refer to a material capable of transporting, releasing, and/or complexing at least one bioactive agent.

As used herein, the term "cartilage" refers to a specialized type of dense connective tissue consisting of cells embedded in a matrix. There are several kinds of cartilage. Translucent cartilage having a homogeneous matrix containing collagenous fibers is found in articular cartilage, in costal cartilages, in the septum of the nose, in larynx and trachea. Articular cartilage is hyaline cartilage covering the articular surfaces of bones. Auricular cartilage is cartilage derived from the auricle of the ear. Costal cartilage connects the true ribs and the sternum. Fibrous cartilage contains collagen fibers. Yellow cartilage is a network of elastic fibers holding cartilage cells, which is primarily found in the epiglottis, the external ear, and the auditory tube. Cartilage is tissue made up of extracellular matrix primarily comprised of the organic compounds collagen, hyaluronic acid (a proteoglycan), and chondrocyte cells, which are responsible for cartilage production. Collagen, hyaluronic acid, and water entrapped within these organic matrix elements yield the unique elastic properties and strength of cartilage.

As used herein, the term "chondrogenic cell" refers to any cell which, when exposed to appropriate stimuli, may differentiate and/or become capable of producing and secreting components characteristic of cartilage tissue.

As used herein, the term "function and/or characteristic of a cell" can refer to the modulation, growth, and/or proliferation of at least one cell, such as a progenitor cell and/or differentiated cell, the modulation of the state of differentiation of at least one cell, and/or the induction of a pathway in at least one cell, which directs the cell to grow, proliferate, and/or differentiate along a desired pathway, e.g., leading to a desired cell phenotype, cell migration, angiogenesis, apoptosis, etc.

As used herein, the term "macromer" can refer to any natural polymer or oligomer.

As used herein, the term "polynucleotide" can refer to oligonucleotides, nucleotides, or to a fragment of any of these, to DNA or RNA (e.g., mRNA, rRNA, siRNA, miRNA, tRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, ribonucleoproteins (e.g., iRNPs). The term can also encompass nucleic acids (i.e., oligonucleotides) containing known analogues of natural nucleotides, as well as nucleic acid-like structures with synthetic backbones.

As used herein, the term "polypeptide" can refer to an oligopeptide, peptide, polypeptide, or protein sequence, or to a fragment, portion, or subunit of any of these, and to naturally occurring or synthetic molecules. The term "polypeptide" can also include amino acids joined to each other by peptide bonds or modified peptide bonds, i.e., peptide isosteres, and may contain any type of modified amino acids. The term "polypeptide" can also include peptides and polypeptide fragments, motifs and the like, glycosylated polypeptides, and all "mimetic" and "peptidomimetic" polypeptide forms.

As used herein, the term "cell" can refer to any progenitor cell, such as totipotent stem cells, pluripotent stem cells, and multipotent stem cells, as well as any of their lineage descendant cells, including more differentiated cells. The terms "stem cell" and "progenitor cell" are used interchangeably herein. The cells can derive from embryonic, fetal, or adult tissues. Examples of progenitor cells can include totipotent stem cells, multipotent stem cells, mesenchymal stem cells (MSCs), hematopoietic stem cells, neuronal stem cells, hematopoietic stem cells, pancreatic stem cells, cardiac stem cells, embryonic stem cells, embryonic germ cells, neural crest stem cells, kidney stem cells, hepatic stem cells, lung stem cells, hemangioblast cells, and endothelial progenitor cells. Additional exemplary progenitor cells can include de-differentiated chondrogenic cells, chondrogenic cells, cord blood stem cells, multi-potent adult progenitor cells, myogenic cells, osteogenic cells, tendogenic cells, ligamentogenic cells, adipogenic cells, and dermatogenic cells.

As used herein, the term "mature chondrocyte" refers to a differentiated cell involved in cartilage formation and repair. Mature chondrocytes can include cells that are capable of expressing biochemical markers characteristic of mature chondrocytes, including, but not limited to, collagen type II, chondroitin sulfate, keratin sulfate, and characteristic morphologic markers including, but not limited to, rounded morphology observed in culture and in vitro generation of tissue or matrices with properties of cartilage.

As used herein, the term "immature chondrocyte" refers to any cell type capable of developing into a mature chondrocyte, such as a differentiated or undifferentiated chondrocyte as well as mesenchymal stem cells that can potentially differentiate into a chondrocyte Immature chondrocytes can include cells that are capable of expressing biochemical and cellular markers characteristic of immature chondrocytes, including, but not limited to, type I collagen, cathepsin B, modifications of the cytoskeleton, and formation of abundant secretory vesicles.

As used herein, the term "tracheal cartilage defect" refers to any tracheal defect of, or injury to, the trachea. Tracheal cartilage defects may be caused by a variety of factors including, but not limited to, stenosis caused by implanted prosthetic devices, penetrating or blunt trauma, and tumors. Additionally, tracheal cartilage defects may be caused by congenital defects ranging from the complete absence of the trachea to an incomplete or malformed trachea.

As used herein, the term "subject" can refer to any animal, including, but not limited to, humans and non-human animals (e.g., rodents, arthropods, insects, fish (e.g., zebrafish)), non-human primates, ovines, bovines, ruminants, lagomorphs, porcines, caprines, equines, canines, felines, ayes, etc.), which is to be the recipient of a particular treatment. Typically, the terms "patient" and "subject" are used interchangeably herein in reference to a human subject.

As used herein, the terms "inhibit," "silencing," and "attenuating" can refer to a measurable reduction in expression of a target mRNA (or the corresponding polypeptide or protein) as compared with the expression of the target mRNA (or the corresponding polypeptide or protein) in the absence of an interfering RNA molecule of the present invention. The reduction in expression of the target mRNA (or the corresponding polypeptide or protein) is commonly referred to as "knock-down" and is reported relative to levels present following administration or expression of a non-targeting control RNA.

As used herein, the term "aggregate" can refer to a group or cluster comprising at least two or more cells (e.g., progenitor and/or differentiated cells).

As used herein, the term "population" can refer to a collection of cells, such as a collection of progenitor and/or differentiated cells.

As used herein, the term "differentiated" as it relates to the cells of the present invention can refer to cells that have developed to a point where they are programmed to develop into a specific type of cell and/or lineage of cells. Similarly, "non-differentiated" or "undifferentiated" as it relates to the cells of the present invention can refer to progenitor cells, i.e., cells having the capacity to develop into various types of cells within a specified lineage or in different lineages.

Embodiments described herein relate to engineered tissue constructs, such as engineered tissue rings, sheets, and disks, systems and methods of forming modular engineered tissue constructs and to the use of modular engineered tissue constructs in modular tissue assembly systems for tissue repair and bio-artificial tissue engineering applications, such as engineered trachea constructs, engineered bone constructs, engineered vascular constructs. The engineered tissue constructs can include self-assembled, scaffold-free, cell aggregates with defined shapes, e.g., rings, disks, or blocks, that are formed by culturing a plurality of cells and nanoparticles and/or microparticles in wells with defined shapes, e.g., rings, disks, or blocks, of a cell culture apparatus or bioreactor. In some embodiments, the self-assembled, cell aggregate can include a population or plurality of cells and plurality of nanoparticles and/or microparticles that are incorporated within the cell aggregate. The nanoparticles and/or microparticles can act as a bulking agent within the cell aggregate to increase the cell aggregate size and/or thickness. Incorporation of the nanoparticles and/or microparticles in the cell aggregate can also improve the mechanical properties of the cell aggregate formed from the cells and nanoparticles and/or microparticles allowing the cell aggregate to be readily manipulated and formed into engineered tissue constructs, such as cartilage rings, bone implants, and/or vascular rings. The nanoparticles and/or microparticles can also include at least one bioactive agent that is differentially and/or controllably released by the nanoparticles and/or microparticles.

The engineered tissue constructs can be used in a modular tissue assembly system to engineer human tissue containing, for example, engineered cartilaginous, bone, and/or vascular segments. The tissue assembly system can permit fusion of self-assembled, scaffold-free, cell aggregates with defined shapes together to generate modular tissue constructs with multiple types of tissues in a spatially-controlled pattern. Culture of the self-assembled, scaffold-free, cell aggregates with defined shapes together in a hollow organ bioreactor can permit further modification of the constructs, including, for example, epithelialization of a surface of the construct.

Advantageously, the tissue assembly system can provide modular control over macroscopic tissue assembly by integration of individual shaped tissue modules of different cell types, permit controlled spatial and temporal presentation of bioactive agents to cells in the constructs, and produce constructs of various sizes and geometries using customizable wells. In one example, engineered trachea constructs can be formed from engineered cartilage rings and perivascular rings and be used to rapidly fill a tracheal defect in vivo. The engineered trachea constructs can avoid tissue granulation, implant migration and restenosis seen in acellular tracheal prostheses, overcome challenges regarding polymer degradation rates and byproducts presented by some scaffold-based approaches, as well as increase cell-cell interactions to help recapitulate de novo tissue formation by eliminating the need for a scaffold. In some embodiments, the engineered trachea constructs can utilize cells that are all of human origin and have the potential for autologous application, circumventing immune issues, potential disease transmission and the need for donor tissue.

FIG. 1 is a schematic illustration of an example of an engineered tissue construct with a defined shape in accordance with an embodiment of the application. The engineered tissue construct 10 has a ring-shape and includes an engineered tissue wall 12 with an inner annular surface 14 and outer annular surface 16 that extend along an axis 18 between a first end 20 and a second end 22 of the tissue wall 12. The outer annular surface 16 defines an outer surface of the engineered tissue ring 10, and the inner annular surface 14 defines an inner lumen 24 of the cartilage ring 10.

The outer annular surface 16 can be substantially parallel to the inner annular surface 14 to provide the tissue wall 12 and engineered tissue ring 10 with a substantially uniform thickness. The thickness of the tissue wall 12 as well as the diameter and length of the tissue ring 10 can be readily tailored and/or engineered for particular bioengineering applications. For example, the diameter of the tissue ring 10 can be at least about 0.1 mm, about 0.5 mm, about 2 mm, about 3 mm, about 4 mm, about 5 mm, about 6 mm, about 7 mm, about 8 mm, about 9 mm, about 10 mm, about 11 mm, about 12 mm about 13 mm, about 14 mm, about 15 mm, about 20 mm, about 30 mm, about 40 mm, about 50 mm, about 75 mm about, about 100 mm or more. The length of the tissue ring can be about 0.1 mm, about 0.5 mm, about 2 mm, about 3 mm, about 4 mm, about 5 mm, about 6 mm, about 7 mm, about 8 mm, about 9 mm, about 10 mm, about 11 mm, about 12 mm about 13 mm, about 14 mm, about 15 mm, about 20 mm, about 30 mm, about 40 mm, about 50 mm, about 75 mm about, about 100 mm or more. The thickness of the tissue ring can be about 0.1 mm, about 0.5 mm, about 2 mm, about 3 mm, about 4 mm, about 5 mm, about 6 mm, about 7 mm, about 8 mm, about 9 mm, about 10 mm, about 11 mm, about 12 mm about 13 mm, about 14 mm, about 15 mm, about 20 mm, or more.

While the outer surface and the inner surface 12 and 14 are depicted as being substantially circular, the outer surface and inner surface 12 and 14 can have other geometries including ellipsoid, toroid, frustoconical, and/or other polygonal geometries. As discussed below, the geometry of the inner surface and the outer surface 12 and 14 of the engineered tissue ring 10 can be defined by the dimensions of the well used to form the engineered tissue ring 10.

It will be appreciated that the engineered tissue construct can have other shapes besides annular or ring shapes. These other shapes can include, for example, disc shapes, wedge shapes, ellipsoid shapes, and other polygonal shapes. The constructs can also include various cavities, holes, and/or lumens. As discussed below, the specific shape of the engineered tissue construct can be defined by the shape of the well used to culture and form the engineered tissue construct.

The engineered tissue ring includes a self-assembled, scaffold-free high density cell aggregate that is formed by culturing a plurality of cells and nanoparticles and/or microparticles in an annular well of a cell culture apparatus or bioreactor. By high density cell aggregates, it is meant the cell aggregate has a cell density of at least about $1\times10^5$ cells/ml in cell growth medium, for example, at least about $1\times10^6$ cells/ml, at least about $1\times10^7$ cells/ml, at least about $1\times10^8$ cells/ml, at least about $1\times10^9$ cell/ml, or at least about $1\times10^{10}$ cell/ml in cell growth medium.

By scaffold-free, it is meant the cells are not seeded in a natural or artificial continuous polymer matrix scaffold that defines the area or volume or at least a portion of the area or volume of the cell aggregate. A scaffold-free cell aggregate as used herein is meant to distinguish the cell aggregate from engineered tissue constructs in which the cells are seeded or embedded into a continuous polymer matrix or scaffold, such as a hydrogel, that encompasses the cells. In contrast, a scaffold-free cell aggregate can include discrete or regions of polymer or matrix materials that are intermixed with the cells and can be in the form of nanoparticles and/or microparticles.

By self-assembled, it is meant that the cells can aggregate or assemble spontaneously or by themselves and without mechanical manipulation while in culture into cell aggregates having defined shapes. Such assembly can be caused by cell-cell interactions, interactions with the particles, or formation of a self-secreted extracellular matrix that can bind to or permit the adhesion of cells in the aggregate.

In some embodiments, the self-assembled, scaffold-free, high density cell aggregate can include a population of cells and a plurality of nanoparticles and/or microparticles that are dispersed with the cells within the cell aggregate. The cell aggregate can also include extracellular matrix material that is secreted by the cells and adheres or binds the cells and nanoparticles and/or microparticles. In some embodiments, the extracellular matrix can include collagen; proteoglycan; glycoprotein; glycosaminoglycan (GAG); as well as other extracellular matrix proteins.

The cells used to form the cell aggregate can be autologous, xenogeneic, allogeneic, and/or syngeneic. Where the cells are not autologous, it may be desirable to administer immunosuppressive agents in order to minimize immunorejection. The cells employed may be primary cells, expanded cells, or cell lines, and may be dividing or non-dividing cells. Cells may be expanded ex vivo prior to mixing with the nanoparticles and/or microparticles. For example, autologous cells can be expanded in this manner if a sufficient number of viable cells cannot be harvested from the host subject. Alternatively or additionally, the cells may be pieces of tissue, including tissue that has some internal structure. The cells may be primary tissue explants and preparations thereof, cell lines (including transformed cells), or host cells.

In some embodiments, the cell can be an undifferentiated or substantially differentiated progenitor cell, such as mesenchymal stem cells, immature chondrocytes, or mature chondrocytes, human umbilical vein, endothelial cells (hU-VEC), and smooth muscle cells. In other embodiments, the progenitor cell can be an adult stem cell, such as a mesenchymal stem cell. The stem cells can be isolated from animal or human tissues. The stem cell used for the production of the engineered cartilage ring can be autologous or allogeneic. In the embodiments described herein, the stem cell can isolated from, but not limited to, tendon/ligament tissue, bone morrow, adipose tissue or dental pulp. The cell aggregate can include at least about 50%, at least about 60%, at least about 70%, at least about 80% cells based on the total volume of the cell aggregate.

The nanoparticles and/or microparticles dispersed with the cells can act as a bulking agent within the cell aggregate to increase the cell aggregate size (e.g., thickness). Incorporation of the nanoparticles and/or microparticles in the cell aggregate can also improve the mechanical properties (e.g., compressive equilibrium modulus and tensile strength) of the cell aggregate and enable more uniform extracellular matrix deposition compared to cell aggregates without the nanoparticles and/or microparticles. This allows the tissue rings formed from the cell aggregate to be readily manipulated and formed into tissue implants, such as trachea implants with defined architectures. The nanoparticles and/or microparticles can also potentially enhance cell function, such as differentiation, and/or enhance or accelerate tissue formation.

The nanoparticles and/or microparticles that are dispersed in the cell aggregate can be formed from a biocompatible and biodegradable material that is capable of improving properties of the cell aggregate and which upon degradation is substantially non-toxic. The microparticles can have a diameter less than about 1 nm and typically between about 1 nm and about 200 μm, e.g., about 20 μm to about 100 μm. The nanoparticles and/or microparticles can include nanospheres, nanocapsules, microspheres, and microcapsules, and may have an approximately spherical geometry and be of fairly uniform size. The size and shape of the nanoparticles and/or microparticles dispersed in the cell aggregate can vary to adjust the mechanical properties of the cell aggregate and tissue construct formed from the cell aggregate. In some embodiments, the nanoparticles and/or microparticles dispersed in the cell aggregate can have substantially uniform diameters; while in other embodiments, the diameters of the dispersed nanoparticles and/or microparticles can vary.

The nanoparticles and/or microparticles can include nanospheres and/or microspheres that have a homogeneous composition as well as nanocapsules and/or microcapsules, which include a core composition (e.g., a bioactive agent) distinct from a surrounding shell. For the purposes of the present invention, for the purposes of the present invention, the terms "nanosphere," "nanoparticle," and "nanocapsule" may be used interchangeably, and the terms "microsphere," "microparticle," and "microcapsule" may be used interchangeably.

In some embodiments, the nanoparticles and/or microparticles can be formed from a biocompatible and biodegradable polymer. Examples of biocompatible, biodegradable polymers include natural polymers, such as collagen, fibrin, gelatin, glycosaminoglycans (GAG), poly (hyaluronic acid), poly(sodium alginate), alginate, hyaluronan, and agarose. Other examples of biocompatible, biodegradable polymers are poly(lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and poly(lactide)s or poly(lactide-co-glycolide)s, biodegradable polyurethanes, and blends and/or copolymers thereof.

Still other examples of materials that may be used to form nanoparticles and/or microparticles can include chitosan, poly(ethylene oxide), poly (lactic acid), poly(acrylic acid), poly(vinyl alcohol), poly(urethane), poly(N-isopropyl acrylamide), poly(vinyl pyrrolidone) (PVP), poly (methacrylic acid), poly(p-styrene carboxylic acid), poly(p-styrenesulfonic acid), poly(vinylsulfonicacid), poly(ethyleneimine), poly(vinylamine), poly(anhydride), poly(L-lysine), poly(L-glutamic acid), poly(gamma-glutamic acid), poly(carprolactone), polylactide, poly(ethylene), poly(propylene), poly (glycolide), poly(lactide-co-glycolide), poly(amide), poly (hydroxylacid), poly(sulfone), poly(amine), poly (saccharide), poly(HEMA), poly(anhydride), polyhydroxybutyrate (PHB), copolymers thereof, and blends thereof.

In some embodiments, the biocompatible and biodegradable polymer is a biodegradable hydrogel, such as gelatin. The biodegradable hydrogel can include a plurality of natural macromers that can be cross-linked using a cross-linking agent to provide a plurality of cross-links. Various sugar derivatives, such as glyoxal, D-ribose, or genipin can be used to cross-link the hydrogel. Other cross-linking agents, such as glutaraldehyde, can also be used. Concentrations of the crosslinking agent as well as time and temperature used for crosslinking can be varied to obtain the optimal results The number or percentage of cross-links linking the macromers can be varied to control the mechanical properties, swelling ratios, and degradation profiles of the hydrodgel and nanoparticles and/or microparticles. The percentage of cross-links can be varied between about 1% and about 70% by weight, and, for example, between about 20% and about 75% by weight. By increasing the percentage of cross-links, for example, the degradation rate of the biodegradable hydrogel can be decreased. Additionally, the compressive stiffness of the biodegradable hydrogel can be increased by increasing the percentage of cross-links. Further, the swelling behavior of the biodegradable hydrogel can be increased by decreasing the percentage of cross-links. It should also be appreciated that the macromer scaffold can be in either a hydrated or lyophilized state to enhance the addition of bioactive agents.

The nanoparticles and/or microparticles can also be modified to enhance cell function, such as differentiation, and/or enhance or accelerate tissue formation as promote cell adhesion. For example, the nanoparticles and/or microparticles can include at least one attachment molecule to facilitate attachment of at least one cell thereto. The attachment molecule can include a polypeptide or small molecule, for example, and may be chemically immobilized onto nanoparticles and/or microparticles to facilitate cell attachment. Examples of attachment molecules can include fibronectin or a portion thereof, collagen or a portion thereof, polypeptides or proteins containing a peptide attachment sequence (e.g., arginine-glycine-aspartate sequence) (or other attachment sequence), enzymatically degradable peptide linkages, cell adhesion ligands, growth factors, degradable amino acid sequences, and/or protein-sequestering peptide sequences. In one example, an attachment molecule can include a peptide having the amino acid sequence of SEQ ID NO: 1 that is chemically immobilized onto the nanoparticles and/or microparticles to facilitate cell attachment.

The nanoparticles and/or microparticles can also be formed from inorganic materials, such as calcium phosphate materials including mineralite, carbonated nano-apatite, calcium phosphate based mineralite, tri-calcium phosphate, octa-calcium phosphate, calcium deficient apatite, amorphous calcium phosphate, hydroxyapatite, substitute apatite, carbonated apatite-like minerals, highly substituted carbonated apatites or a mixture thereof. Calcium phosphate nanoparticles and/or microparticles can have an average particle size of between about 1 nm and about 200 μm. It will be appreciated that smaller or larger calcium phosphate nanoparticles and/or microparticles may be used. The calcium phosphate nanoparticles and/or microparticles can have a generally spherical morphology and be of a substantially uniform size or, alternatively, may be irregular in morphology. Calcium phosphate nanoparticles and/or microparticles may be complexed with surface modifying agents to provide a threshold surface energy sufficient to bind material (e.g., bioactive agents) to the surface of the microparticle without denaturing the material. Non-limiting examples of surface modifying agents can include basic or modified sugars, such as cellobiose, carbohydrates, carbohydrate derivatives, macromolecules with carbohydrate-like components characterized by an abundance of —OH side groups and polyethylene glycol.

In some embodiments, the nanoparticles and/or microparticles can include at least one, two, three, or more bioactive agent(s) that is capable of modulating a function and/or characteristic of a cell. For example, the bioactive agent may be capable of modulating a function and/or characteristic of a cell that is dispersed with the nanoparticles and/or microparticles. Alternatively or additionally, the bioactive agent may be capable of modulating a function and/or characteristic of an endogenous cell surrounding a tissue construct formed of the cell aggregate implanted in a tissue defect.

In some embodiments, the at least one bioactive agent can include, for example, polynucleotides and/or polypeptides encoding or comprising, for example, transcription factors, differentiation factors, growth factors, and combinations thereof. The at least one bioactive agent can also include any agent capable of promoting cartilage, bone, or tissue formation. Examples of bioactive agents include various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., EGF), HGF, VEGF, fibroblast growth factors (e.g., bFGF), PDGF, insulin-like growth factor (e.g., IGF-I, IGF-II) and transforming growth factors (e.g., TGF-β I-III), parathyroid hormone, parathyroid hormone related peptide, bone morphogenic proteins (e.g., BMP-2, BMP-4, BMP-6, BMP-7, BMP-12, BMP-13, BMP-14), sonic hedgehog, growth differentiation factors (e.g., GDF5, GDF6, GDF8), recombinant human growth factors (e.g., MP-52 and the MP-52 variant rhGDF-5), cartilage-derived morphogenic proteins (CDMP-1, CDMP-2, CDMP-3), small molecules that affect the upregulation of specific growth factors, tenascin-C, hyaluronic acid, chondroitin sulfate, fibronectin, decorin, thromboelastin, thrombin-derived peptides, heparin-binding domains, heparin, heparin sulfate, polynucleotides, DNA fragments, DNA plasmids, MMPs, TIMPs, interfering RNA molecules, such as siRNAs, miRNAs, DNA encoding for an shRNA of interest, oligonucleotides, proteoglycans, glycoproteins, and glycosaminoglycans.

It will be appreciated at least one or more bioactive agent can be incorporated on or within at least one microparticle. The at least one microparticle can differentially or controllably release the at least one bioactive agent or be taken up (e.g., via endocytosis) by at least one cell to modulate the function and/or characteristic of the cell, such as to promote cartilage formation. The at least one bioactive agent may be at least partially coated on the surface of the at least one microparticle. Alternatively, the at least one bioactive agent may be dispersed, incorporated, and/or impregnated within the microparticle. For example, a bioactive agent comprising a DNA plasmid (e.g., a plasmid encoding BMP-2) can be coated onto the surface of the microparticle. After forming the nanoparticles and/or microparticles with the bioactive agent, the nanoparticles and/or microparticles can be coated with DNA or protein to prevent nanoparticle aggregation and/or promote cellular uptake. It will be appreciated that one or more of the same or different bioactive agents can be incorporated on or within the at least one nanoparticles and/or microparticles.

In some embodiments, a bioactive agent can comprise an interfering RNA or miRNA molecule incorporated on or within at least one microparticle dispersed on or within the cell aggregate. The interfering RNA or miRNA molecule can include any RNA molecule that is capable of silencing an mRNA and thereby reducing or inhibiting expression of a polypeptide encoded by the target mRNA. Alternatively, the interfering RNA molecule can include a DNA molecule encoding for a shRNA of interest. For example, the interfering RNA molecule can comprise a short interfering RNA (siRNA) or microRNA molecule capable of silencing a target mRNA that encodes any one or combination of the polypeptides or proteins described above. The at least one microparticle can differentially or controllably release the at least one interfering RNA molecule or be taken up (e.g., via endocytosis) by at least one cell to modulate a function and/or characteristic of the cell.

The type, distribution, size, and/or crosslinking of the nanoparticles and/or microparticles can also be modified or configured to differentially, controllably, spatially, and/or temporally release at least one bioactive agent in the cell aggregate. In some embodiments, individual nanoparticles and/or microparticles can be formed of different materials or components, such as different polymers having different molecular weights or cross-linking. Moreover, the nanoparticles and/or microparticles can be formed into particular shapes or form to facilitate release of one or more bioactive agents according to a specific temoral release profile. Alternatively, one or more materials or agents can be added to the nanoparticles and/or microparticles to facilitate differential and/or controlled release of one or more bioactive agents according to a temporal release profile. For example, during formation of the nanoparticles and/or microparticles, the concentration of bioactive molecules incorporated into the nanoparticles and/or microparticles can be increased or decreased to increase or decrease the concentration of the bioactive molecules upon release from the nanoparticles and/or microparticles.

In some embodiments, the cell aggregate can include a plurality of first nanoparticles and/or microparticles that can include or release one or more first bioactive agent(s) and a plurality of second nanoparticles and/or microparticles that can include or release one or more second bioactive agent(s). The one or more first bioactive agents and the one or more second bioactive agents may comprise the same or different agents. The one or more first bioactive agents and the one or more second bioactive agents can be differentially, sequentially, and/or controllably released from the first nanoparticles and/or microparticles and second nanoparticles and/or microparticles to modulate a different function and/or characteristic of a cell. It will be appreciated that the one or more first bioactive agents can have a release profile that is the same or different from the release profile of the one or more second bioactive agents from the first nanoparticles and/or microparticles and the second nanoparticles and/or microparticles. Additionally, it will be appreciated that the first nanoparticles and/or microparticles can degrade or diffuse before the degradation or diffusion of the second nanoparticles and/or microparticles or allow for an increased rate of release or diffusion of the one or more first bioactive agents compared to the release of the one or more second bioactive agents. The first and second nanoparticles and/or microparticles may be dispersed uniformly on or within the cell aggregate or, alternatively, dispersed such that different densities of the first nanoparticles and/or microparticles and second nanoparticles and/or microparticles are localized on or within different portions of the cell aggregate.

In some embodiments, the self-assembled, scaffold-free cell aggregate can be formed by combining the nanoparticles and/or microparticles with the cells and then suspending the cells and the nanoparticles and/or microparticles in a culture medium. The nanoparticles and/or microparticles can be formed, for example, from a hydrogel, such as gelatin, that is cross-linked with a cross-linking agent, (e.g., genipin). In some instances, the nanoparticles and/or microparticles can have a diameter of about 20 um to about 100 um and a degree of crosslinking of about 20% to about 70%. The nanoparticles and/or microparticles can also include a growth factor, such as TGFB1, that can be loaded in the nanoparticles and/or microparticles and controllably released from the nanoparticles and/or microparticles. Cell aggregates incorporated with fast degrading nanoparticles and/or microparticles containing TGF-β1 produced significantly more GAG and GAG per DNA.

Figure 2:
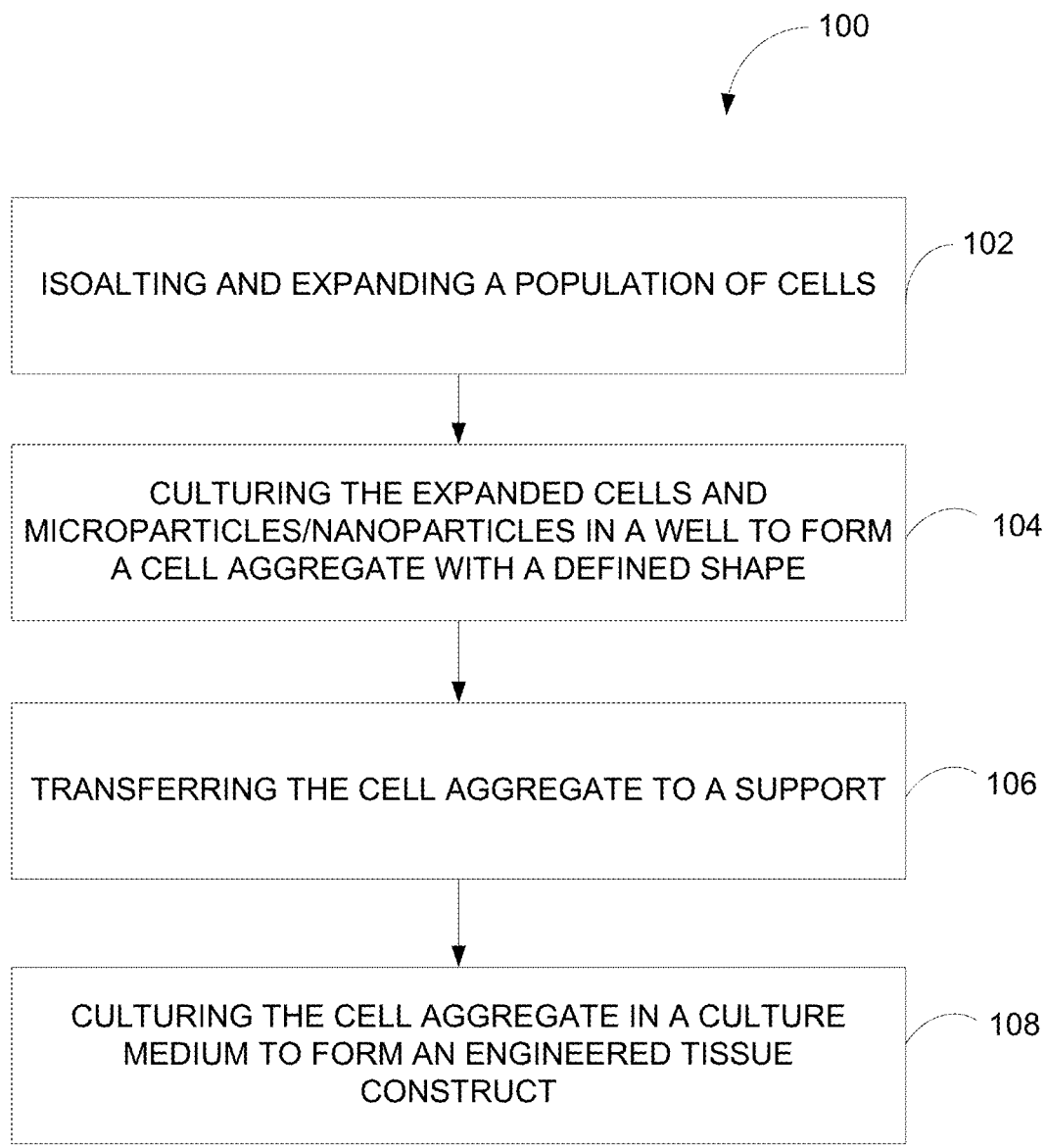
FIG. 2 is a flow diagram showing a method of forming an engineered tissue construct.

FIG. 2 is a schematic illustration of a method 100 of forming an engineered tissue construct that includes at least one self-assembled cell aggregate. In the method, at step 102, a population of cells can be isolated and expanded.

The cells can include any totipotent stem cell, pluripotent stem cell, or multipotent stem cell, and/or differentiated cell. Progenitor cells can include autologous cells; however, it will be appreciated that xenogeneic, allogeneic, or syngeneic cells may also be used. The progenitor cells employed may be primary cells, expanded cells or cell lines, and may be dividing or non-dividing cells. The cells can be derived from any desired source. For example, the cells may be derived from primary tissue explants and preparations thereof, cell lines (including transformed cells) that have been passaged once (P1), twice (P2), or even more times, or host cells (e.g., human hosts). Any known method may be employed to harvest cells for use in the present invention. For example, mesenchymal stem cells, which can differentiate into a variety of mesenchymal or connective tissues (e.g., adipose tissue, osseous tissue, cartilaginous tissue, elastic tissue, and fibrous connective tissues), can be isolated according to the techniques disclosed in U.S. Pat. No. 5,486,359 to Caplan et al. and U.S. Pat. No. 5,226,914 to Caplan et al., the entireties of which are hereby incorporated by reference. In one example, the population of cells can comprise a population of human mesenchymal stem cells.

The cells used to form the cell aggregate can include a mixture of different populations of cells or different phenotypes of cells to modulate the properties of the engineered tissue ring. For example, the cell aggregate that forms the cartilage ring can include mixture of chondrogenic cells, such as mesenchymal stem cells, vascular progenitor cells, such as human umbilical vein endothelial cells, and/or smooth muscle cells.

In one example, the population of cells can comprise a population of chondrogenic cells, such as human mesenchymal stem cells. Chondrogenic cells may be isolated directly from pre-existing cartilage tissue such as hyaline cartilage, elastic cartilage, or fibrocartilage. More specifically, chondrogenic cells may be isolated from articular cartilage (from either weight-bearing or non-weight-bearing joints), costal cartilage, nasal cartilage, auricular cartilage, tracheal cartilage, epiglottic cartilage, thyroid cartilage, arytenoid cartilage, and/or cricoid cartilage. Alternatively, chondrogenic cells may be isolated from bone marrow or an established cell line.

Chondrogenic cells may be allogeneic, autologous, or a combination thereof, and may be obtained from various biological sources. Biological sources may include, for example, both human and non-human organisms. Non-human organisms contemplated by the present invention include primates, livestock animals (e.g., sheep, pigs, cows, horses, donkeys), laboratory test animals (e.g., mice, hamsters, rabbits, rats, guinea pigs), domestic companion animals (e.g., dogs, cats), birds (e.g., chicken, geese, ducks, and other poultry birds, game birds, emus, ostriches), captive wild or tamed animals (e.g., foxes, kangaroos, dingoes), reptiles and fish.

After obtaining a tissue biopsy of auricular cartilage, for example, the chondrogenic cells may be released by contacting the tissue biopsy with at least one agent capable of dissociating the chondrogenic cells. Examples of agents that can be used include trypsin and collagenase enzymes. For example, a tissue biopsy may be sequentially digested in about 0.25% trypsin/EDTA for about 30 minutes, about 0.1% testicular hyaluronidase for about 15 minutes, and about 0.1% collagenase type II for about 24 hours. The digestion may be carried out at about 37° C. in about a 20 ml volume. Any undigested tissue and/or debris can be removed by filtering the cell suspension using a Nitex 70 μm sterile filter followed by centrifugation. The viability of the cells can be assessed by Trypan Blue dye exclusion test. By digesting the tissue biopsy, a population of chondrogenic cells comprising mature chondrocytes, immature chondrocytes, or a combination thereof, may be successfully isolated from the tissue biopsy.

The isolated population of cells may next be expanded in a conditioned growth media effective to promote expansion of the cells. For example, once the chondrogenic cells have been isolated from the tissue biopsy, they may be proliferated ex vivo in monolayer culture using conventional techniques well known in the art. Briefly, the chondrogenic cells may be passaged after the cells have proliferated to such a density that they contact one another on the surface of a cell culture plate. During the passaging step, the cells may be released from the substratum. This may be performed by routinely pouring a solution containing a proteolytic enzyme, such as trypsin, onto the monolayer. The proteolytic enzyme hydrolyzes proteins which anchor the cells on the substratum and, as a result, the cells may be released from the surface of the substratum.

After isolation and expansion of the cells, the cells can be provided in a culture medium and mixed with nanoparticles and/or microparticles. In some embodiments, the culture medium can also include bioactive agents that promote tissue formation. The nanoparticles and/or microparticles may be dispersed with cells in the suspension in a substantially uniform manner. The culture medium can promote self-assembly of cell aggregates comprising the cells and nanoparticles and/or microparticles. In example, the culture medium can include chemically defined basal pellet medium (BPM) and an amount of TGF-β1 effective to stimulate cell growth and aggregation.

At step 104, the suspension can then be provided in a well, vessel, and/or chamber of a culture apparatus with a defined shape, geometry, and/or architecture. The shape of the well can define the shape of the self-assembled cell aggregate and engineered tissue construct. In one example, the well of the culture apparatus can have an annular shape and include an annular post. An outer surface of the annular post can be used to define an inner surface of a tissue ring so formed. The well of the culture apparatus can be formed from a biocompatible material, such as agarose, that promotes self-assembly of the cell aggregates. In one example, the agarose well can be formed by molding agarose with negative molds of machined or 3-D printed polydimethylsiloxane (PDMS).

The density at which the cells are seeded into the wells of the culture vessel can be, for example, about $1 \times 10^5$ cells/mL to about $100 \times 10^6$ cells/mL.

The cells and nanoparticles and/or microparticles can be cultured at a temperature and atmosphere effective to promote formation of a self-assembled cell aggregate that has a shape defined by the well. For example, the cells may be cultured at a temperature of about 37° C. in an atmosphere of about 5% carbon dioxide at an about 90% to about 95% humidity. The oxygen percentage can be varied from about 1% to about 21%. Typically, the cells can be cultured for about 1 day to about 3 or more weeks.

Following self-assembly of the cell aggregate, at step 106, one or more of the self assembled cell aggregates can be transferred from the well onto a support. In one example, where the self-assembled cell aggregate is in the shape of a ring, the ring-shaped self-assembled cell aggregate can be transferred onto a cylindrical support or tube such that the support extends through a lumen of the ring-shaped cell aggregate(s). The support can be made of a biocompatible material, such as silicone and have a diameter and shape substantially the same or similar to the diameter of the lumen of the ring-shaped cell aggregate(s).

At step 108, the cell aggregate(s) positioned on the support can then be provided in a cell differentiation medium, such as a chondrogenic induction medium, in a cell culture vessel and cultured under conditions designed to promote cell differentiation, e.g., cartilage formation. The cells can be cultured at about 37° C. in about a 5% carbon dioxide atmosphere at about 90% to about 95% humidity. The oxygen percentage can be varied from about 1% to about 21%. Cell differentiation medium, can be changed daily or as needed and/or replaced with other cell culture medium, such as osteogenic induction to promote bone formation. Other cell culture mediums can also be used, such as angiogenic medium or vasculogenic medium. The cell aggregate(s) can be cultured for a duration of time effective to promote tissue formation, for example, from about 1 week to about 4 or more weeks.

During culturing, bioactive agent(s), such as TGF-β1 and/or BMP-2, can be released from the nanoparticles and/or microparticles via diffusion and/or as the nanoparticles and/or microparticles begin to degrade. Controlled release of the bioactive agent from the particles may be dependent on the size and composition of the nanoparticles and/or microparticles, as well as the composition of the medium in which the aggregate is immersed. For example, the release rate of the bioactive agent(s) can be selectively controlled by changing the degree or percent of crosslinking of the polymers used to form the nanoparticles and/or microparticles, the size of the nanoparticles and/or microparticles, and the amount of bioactive agent that is loaded into the nanoparticles and/or microparticles.

It will be appreciated that other bioactive agents can also be added to the medium to enhance or stimulate cell growth. Examples of other bioactive agents include growth factors, such as transforming growth factor-β(TGF-β) (e.g., TGF-β1 or TGF-β3), platelet-derived growth factor, insulin-like growth factor, acid fibroblast growth factor, basic fibroblast growth factor, epidermal growth factor, hepatocytic growth factor, keratinocyte growth factor, and bone morphogenic protein. It will also be appreciated that other agents, such as cytokines, hormones (e.g., parathyroid hormone, parathyroid hormone-related protein, hydrocortisone, thyroxine, insulin), fatty acids (e.g., Omega-3 fatty acids such as α18:3 linolenate), and/or vitamins (e.g., vitamin D), may also be added or removed from the serum-free medium to promote cell growth. Additionally, the engineered constructs can be mechanically stimulated to enhance or stimulate cell growth.

The inclusion of the nanoparticles and/or microparticles in the cell aggregate can allow for substantially more uniform spatial delivery of the bioactive agent throughout the interior of the aggregate. The substantially uniform distribution of the nanoparticles and/or microparticles and relatively uniform release of the bioactive agent in the cell aggregate is advantageous for several reasons, including, but not limited to: (1) rapidly inducing uniform cell differentiation; (2) providing control over the spatial and temporal presentation of bioactive agents; (3) allowing for the use of lower concentrations of bioactive agents as compared to systems employing exogenously-supplied growth factors; (4) enhancing the spatial distribution of extracellular matrix that is formed between the cells; and (5) enhancing the amount of extracellular matrix produced in the cell aggregate. These enhanced properties allows and/or provides for the formation of larger, more mechanically robust tissue constructs.

It will be appreciated that the cell aggregate can further include other nanoparticles and/or microparticles, such as second, third, fourth, or more nanoparticles that include other (e.g., second, third, fourth, or more) bioactive agents. The other bioactive agents may be the same or different type of agent (described above). The other nanoparticles and/or microparticles can differentially, sequentially, and/or controllably release the different bioactive agents to modulate the same or different function and/or characteristics of at least one cell in the aggregate. The bioactive agents can have the same or different release profiles from the first nanoparticles and/or microparticles.

As a result of culturing the cell aggregates with the nanoparticles and/or microparticles, a mechanically robust engineered tissue construct with a defined shape can be formed that can be readily shaped, transferred, and/or manipulated to form the tissue construct. In one example, an engineered tissue ring formed from mesenchymal stem cells can have a glycosaminoglycan (GAG) content that can be substantially equal or similar to the GAG content of native cartilage.

In some embodiments, multiple self-assembled cell aggregates can be fused together to form a modular engineered tissue construct. For example, multiple self-assembled cell aggregates having substantially same composition can be positioned or stacked on a support such that portions of the self-assembled cell-aggregates abut one another on the support. The stacked self-assembled cell-aggregates can be cultured in the culture medium and upon culturing can fuse together to form a continuous substantially homogenous modular engineered tissue construct. After culturing, the continuous substantially homogenous modular engineered tissue construct can be removed from the culture vessel.

In one example, as shown in FIG. 4, multiple ring-shaped cell aggregates having similar shapes formed in an annular well can be positioned or stacked on a support such that adjacent ring-shaped cell-aggregates abut one another on the support. The stacked ring-shaped cell-aggregates can be cultured in a chondrogenic medium and upon culturing can fuse together to form a continuous substantially homogenous engineered tissue tube.

In other embodiments, a heterogenous modular engineered tissue construct can be formed that includes defined regions or portions (e.g., rings) of differing or similar cell aggregate materials. The differing regions or portions of the heterogenous modular engineered tissue construct can be provided or formed with or without nanoparticles and/or microparticles and can have similar or different properties to vary the properties of the tissue construct for particular tissue engineering applications.

In some embodiments, a heterogenous modular tissue construct can be formed by fusing self-assembled cell aggregates formed from different mixtures of cells with or without nanoparticles and/or microparticles. For instance, a first mixture of cells with or without nanopaticles and/or microparticles can be seeded into wells of a culture chamber to form first self-assembled cell aggregates. A second mixture of cells with or without nanoparticles and/or microparticles different than the first mixture can be seeded in the same or separate wells of a culture chamber to form second self-assembled cell aggregates. The first mixture of nanopaticles and/or microparticles and cells can include different type, concentration, amount, and/or distribution, of cells, nanoparticles and/or microparticles and/or potentially bioactive agents as the second mixture of nanopaticles and/or microparticles and cells to vary the compositions and properties of the first self-assembled cell aggregates and the second self-assembled cell aggregates.

The first self-assembled cell aggregates and the second self-assembled cell aggregates can be transferred from the wells onto a support such that portions of the self-assembled cell-aggregates abut one another on the support. In some embodiments, one or more first self-assembled cell aggregates can be alternated with one more second self-assembled cell aggregates on the support such that different self-assembled aggregates are in contact with each other. The first and second self-assembled cell aggregate(s) positioned on the support can then be provided in a cell culture medium in a cell culture vessel and cultured under conditions designed to fuse the separate aggregates and form a modular engineered tissue construct.

It will be appreciated that the heterogenous modular engineered tissue construct can be formed by fusing more than two different types of self-assembled cell aggregates. Each of the different self-assembled cell aggregates can include differing mixtures of cells with or without nanopaticles and/or microparticles and be fused together in any combination, e.g., alternating in series, etc. Additionally, each of the different self-assembled cell aggregates can have different shapes so that engineered tissue constructs formed by fusing the different self-assembled cell aggregates can be provided with complex shapes and geometries.

In one example, as shown in FIG. 3, first ring-shaped cell aggregates formed form a mixture of human mesenchymal stem cells and TGF-β1 loaded microparticles and/or nanoparticles and second ring-shaped cell aggregates formed from smooth muscle cells can be stacked on a support to provide alternating rings of the first ring-shaped cells aggregates and the second ring-shaped aggregates. The first and second ring-shaped cell aggregate(s) positioned on the support can then be provided in a cell culture medium in a cell culture vessel and cultured under conditions designed to fuse the rings and form multi-tissue type hMSC and smooth muscle cell tubes with both cartilaginous and non-cartilaginous portions.

In other examples, first ring-shaped cell aggregates formed form a mixture of human mesenchymal stem cells and TGF-β1 and/or BMP-2 loaded microparticles and/or nanoparticles and second ring-shaped cell aggregates formed from a mixture of human mesenchymal stem cells and human umbilical vein endothelial cells (e.g., a 1:1 mixture of MSCs to hUVEC) can be stacked on a support to provide alternating rings of the first ring-shaped cells aggregates and the second ring-shaped aggregates. The first and second ring-shaped cell aggregate(s) positioned on the support can then be provided in a cell culture medium in a cell culture vessel and cultured under conditions designed to fuse the rings and form multi-tissue type hMSC and hUVEC tubes with both cartilaginous and prevascular portions.

Optionally, a homogenous or heterogeneous modular engineered tissue construct formed by the method described herein can be further modified by seeding cells onto or within the homogenous or heterogeneous modular engineered tissue construct. In one example, where the homogenous or heterogeneous modular engineered tissue construct is in the form of a ring or tube used for a trachea implant, respiratory epithelial cells can be seeded on an inner surface of a lumen of the ring or tube to form a bilayer cell tube or ring. It will be appreciated that other cells or cell types can be seeded onto or within the homogenous or heterogeneous modular engineered tissue construct to modulate the properties of the homogenous or heterogeneous modular engineered tissue construct and form a heterogenous or multilayer structure.

The homogenous or heterogeneous modular engineered tissue construct produced by the method described herein can find use in a variety of applications. One example of such an application can include forming a whole or partial portion of a trachea implant to treat a tracheal defect in a subject. In some embodiments, the tracheal implant can include a heterogeneous cartilage tube with alternating fused cartilaginous and noncartilaginous portions and an inner lumen in which is seeded epithelial cells to provide an epithelial lined implant. Depending upon the clinical needs of the subject, homogenous or heterogeneous cartilage ring or tube produced by the methods described herein may be used to form a whole trachea or only a portion of a whole trachea. For example, a tracheal implant may be formed by first obtaining a homogenous or heterogeneous modular engineered tissue ring or tube that include cartilage rings and/or vascular rings and/or prevascular rings, with or without epithelial cell lining. The tracheal implant may be optimally sized to suit the needs of the subject. The implant may be used to repair a tracheal cartilage defect as described in greater detail below.

Repair of a tracheal cartilage defect may begin by first identifying the defect. Tracheal cartilage defects may be readily identifiable by visually identifying the defects during open surgery of the trachea or, alternatively, by using computer aided tomography, X-ray examination, magnetic resonance imaging, analysis of serum markers, or by any other procedures known in the art.

Once the tracheal cartilage defect has been identified, an appropriately-sized tracheal implant may be selected. For example, the tracheal implant may have a size and shape so that when the tracheal implant is implanted, the edges of the tracheal implant directly contact the edges of native cartilage tissue. The tracheal implant may be fixed in place by, for example, surgically fixing the implant with bioresorbable sutures. Additionally or optionally, the tracheal implant may be fixed in place by applying a bioadhesive to the region interfacing the tracheal implant and the tracheal cartilage defect. Examples of suitable bioadhesives include fibrin-thrombin glues and synthetic bioadhesives similar to those disclosed in U.S. Pat. No. 5,197,973.

The cartilage tissue defect may comprise a stenotic portion of the trachea, such as two of the cartilages comprising the trachea, caused by prolonged placement of a tracheal T-tube. To repair the tracheal cartilage defect, the stenotic portion may first be surgically excised. Next, a tracheal implant may be formed having a size and shape complementary to the size and shape of the excised stenotic portion. The tracheal implant may then be surgically fixed in place of the excised stenotic portion by an end-to-end anastomosis. After the tracheal implant has been suitably fixed in place, the surgical procedure may be completed and the tracheal implant permitted to integrate into the native cartilage tissue.

In an alternative example, the tracheal cartilage defect may comprise a congenital defect, such as a missing trachea, in a pediatric subject. A tracheal implant comprising a whole trachea may be prepared and then surgically implanted into the subject by an end-to-end anastomosis. After the tracheal implant has been suitably fixed in place, the surgical procedure may be completed and the tracheal implant permitted to integrate into the native tissue. By providing the subject with a whole tracheal implant, the tracheal implant may integrate into the native tissue and grow along with the subject, thus removing the need to perform additional surgeries as the subject ages.

It will be appreciated that the homogenous or heterogeneous modular engineered tissue construct produced by the methods described herein can also be used to form tissue constructs other than engineered trachea. Such tissue constructs can include, for example, vasculature implants for vasculature repair, bone implants that potentially include multiple layers or modular structures, tubular tissues or organs, such as the esophagus, small intestines, urethra, vagina, and muscular tubes (e.g., cardiac and skeletal muscle), other organs or tissue, or other implants used to repair tissue or cartilage defects. Tissue defects in the context of the present invention should also be understood to comprise those conditions where surgical repair of tissue is required, such as cosmetic surgery (e.g., nose, ear). Thus, tissue defects can occur anywhere in the body where tissue formation is disrupted, where tissue is damaged or non-existent due to a genetic defect, where tissue is important for the structure or functioning of an organ (e.g., structures such as menisci, the ear, the nose, the larynx, the trachea, the bronchi, structures of the heart valves, part of the costae, synchondroses, enthuses, etc.), and/or where tissue is removed due to cancer, for example. For such applications, the homogenous or heterogenous modular engineered tissue construct can be shaped, molded, or configured into a variety of configurations.

In still other embodiments, the homogenous or heterogeneous modular engineered tissue construct produced by the methods described herein can be combined with or adhered to other tissue constructs to form a heterogeneous tissue constructs. For example, a modular engineered tissue ring or tube produced by the methods described herein can be provided on, combined with or adhered to demineralized bone matrix to provide and osteochondral tissue construct. The tissue construct can be readily implanted and integrated osteochondral defect.

In other embodiments, the DNA or cells in the homogenous or heterogeneous modular engineered tissue construct produced by the methods described herein can be removed or lysed to provide an acellular tissue construct that includes the extracellular matrix so formed and, potentially, the partially or completely degraded nanoparticles and/or microparticles. Removal may be achieved by, for example, detergent treatment, (e.g., SDS treatment) treatment with DNase and RNase, and/or freeze/thaw cycles. The acellular tissue construct can then be used alone for tissue engineering application or in combination with other cell types or growth factors for the promotion of tissue repair. The acellular tissue construct can be used as an acellular biomaterial for tissue engineering application similar to the above after decellularization. When used alone, the acellular tissue can be used to prevent or repair tissue defects, enhance host cell attachment, infiltration, differentiation, extension, and proliferation. The acellular tissue construct as a decellularized product can be used together with other known bioactive agents and cell types for the promotion of tissue repair.

The following examples are for the purpose of illustration only and are not intended to limit the scope of the claims, which are appended hereto.

Example 1

In this Example a tracheal tissue replacement strategy is demonstrated using a bottom-up approach for production of human MSC (hMSC)-derived cartilaginous rings and tubes through employment of custom designed culture wells and an assembly system. This technology is then used to test the hypothesis that incorporation of chondrogenic growth factor-delivering microspheres into the ring and tube-shaped high-cell density constructs enhances chondrogenesis with regard to mechanical properties and matrix production and distribution to provide functional tracheal patency in future clinical applications.

Methods

EXPERIMENTAL DESIGN

The work described here investigated the formation of engineered cartilaginous rings and tubes in custom designed molds. hMSCs alone ("hMSC") or with bioactive factor-releasing biopolymer microspheres ("hMSC+MS") were seeded in annular agarose wells to form scaffold-free self-assembled three-dimensional tissue rings. Subsequently, tissue rings were stacked in 3-ring or 6-ring conformations to fuse into tissue tubes. Chondrogenesis was induced in rings and tubes during 22 days of in vitro culture after which constructs were harvested for analysis. A schematic of the ring and tube formation procedure is shown in FIG. 4.

hMSC Isolation and Culture hMSCs were isolated from bone marrow aspirates obtained from the Case Comprehensive Cancer Center Hematopoietic Biorepository and Cellular Therapy Core under University Hospitals of Cleveland Institutional Review Board approval, as previously described. Briefly, bone marrow aspirates were washed with expansion media (Dulbecco's Modified Eagle's Mediumelow glucose (DMEM-LG; Sigma-Aldrich, St. Louis, Mo.)) containing 10% pre-screened bovine serum (Gibco Qualified FBS; Life Technologies, Carlsbad, Calif.). Mononuclear cells were separated using a Percoll gradient (Sigma-Aldrich), plated in expansion media and cultured in a 37° C. humidified incubator with 5% $CO_2$. Non-adherent cells were washed away during the first media change. Adherent cells received fresh expansion media supplemented with 10 ng/ml fibroblast growth factor-2 (FGF-2, R&D Systems, Minneapolis, Minn.) every 2-3 days. The hMSCs were subcultured at ~90% confluence, and passage 3 cells were used in this study.

Microsphere Synthesis and Characterization

Gelatin microspheres (11.1 w/v % Type A; Sigma-Aldrich) were synthesized in a water-in-oil emulsion, as previously described, with slight modifications. Microspheres were crosslinked with 1 w/v % genipin for 3 h (Wako Chemicals USA Inc., Richmond, Va.), washed with deionized $H_2O$, lyophilized and rehydrated with Dulbecco's Phosphate Buffered Saline (PBS; HyClone Laboratories, Logan, Utah) containing 400 ng TGF-b1 (PeproTech, Rocky Hill, N.J.) per mg microspheres. Light microscopy images of hydrated, crosslinked microspheres (N=268) were acquired on a TMS microscope (Nikon, Tokyo, Japan) with a Coolpix 995 camera (Nikon) to determine microsphere diameters, which were measured using NIH Image J analysis software. The degree of microsphere crosslinking was quantified via a ninhydrin assay, based on a previously described protocol. Here, the ninhydrin solution was added to dry microspheres and incubated for 2.5 min.

Cell Culture Well Preparation

Agarose molds for cell culture were prepared as follows. Briefly, a polycarbonate sheet (Small Parts Inc., Miramar, Fla.) was machined to contain annular wells with concentric 2 mm diameter posts surrounded by a 3.75 mm wide trough. A polydimethylsiloxane (PDMS; Sylgard 184, Dow Corning, Midland, Mich.) negative mold of the polycarbonate template was cured and steam autoclaved for sterilization. Two percent w/v agarose (Denville Scientific Inc., Metuchen, N.J.) in DMEM-LG was autoclaved and used to fill the PDMS mold. After cooling, the ring-shaped culture wells were removed from the PDMS mold, moved into 6-well plates (BD, Franklin Lakes, N.J.) and incubated overnight in basal pellet medium (BPM) comprised of Dulbecco's Modified Eagle's Medium, high glucose (DMEM-HG; Sigma Aldrich), 1% ITS p Premix (Corning Inc, Corning, N.Y.), $10^{-7}$ M dexamethasone (MP Biomedicals, Solon, Ohio), 1 mM sodium pyruvate (HyClone Laboratories), 100 μM non-essential amino acids (Lonza Group, Basel, Switzerland), 37.5 μg/ml ascorbic acid-2-phosphate (Wako Chemicals USA Inc.) and 100 μ/ml penicillin-streptomycin (Corning Inc.).

Assembly of Microsphere-Containing Tissue Rings and Tubes

Figure 5:
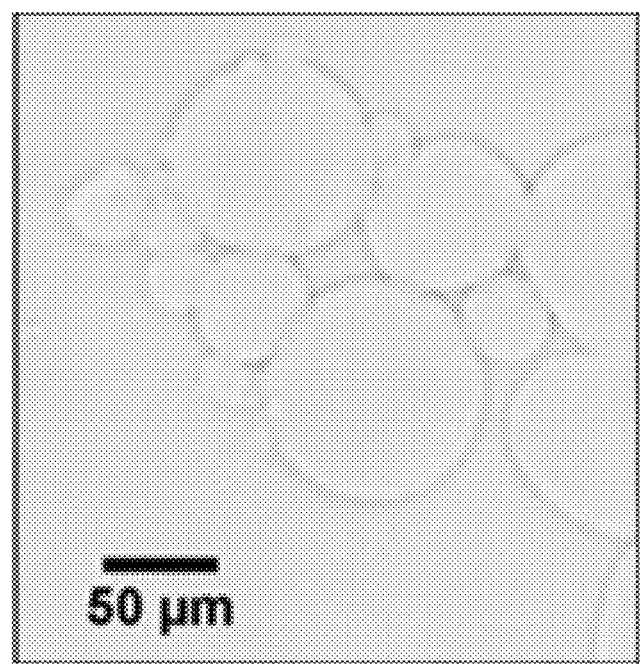
FIG. 5 illustrates a light photomicrograph of crosslinked gelatin microspheres.

Trypsinized hMSCs (400,000 cells) with or without 0.3 mg TGF-β1 laden microspheres in 50 μL media were seeded in a circular fashion in each custom designed annular well. Microsphere-containing tissues ("hMSC+MS") were seeded and cultured in BPM. hMSC-only groups ("hMSC") did not contain microspheres and were seeded and cultured in BPM supplemented with 10 ng/ml TGF-β1. After 24 h, 3 ml of experimental condition-specific media were added to the agarose wells. On day 2, some of the self-assembled rings were transferred from the annular wells onto 2 mm silicone tubes (Specialty Manufacturing Inc., Saginaw, Mich.) to form 3- and 6-ring tissue tubes. Silicone tubes were sandwiched between custom engineered polycarbonate holders and the developing tissue tubes were cultured horizontally in 60 mm petri dishes (BD) containing 4.8e6 million cells and 9 ml of condition specific media. A schematic of the tissue ring and tube assembly processes is shown in FIG. 5. A Galaxy S4 phone camera (Samsung, Seoul, Korea) was used to capture images of the custom culture set-up right after tissue tube assembly. Tissue rings and tubes with and without microspheres were grown in a humidified cell culture incubator at 37° C. and 5% $CO_2$ for 22 days with media changes every 2 and 3 days, respectively.

Gross Morphological Assessment

On day 22 of total culture, rings (22 days of culture as rings) and tubes (2 days of culture as rings followed by 20 days of culture as tubes) were harvested and photographs of all tissues were taken with a Galaxy S4 phone camera. Healthy, native rat tracheas (male NIH Nude rats 14e15 weeks old (N=4); Taconic, Hudson, N.Y.), freshly harvested from rats sacrificed for another study in accordance to a protocol approved by the Institutional Animal Care and Usage Committee at Case Western Reserve University, were used for comparison.

Biochemical Analysis

Tissue rings (N=4) and 3-ring tubes (N=3) were digested in papain solution (Sigma Aldrich) at 65° C. GAG and DNA contents were measured using dimethylmethylene blue (DMMB; Sigma-Aldrich) and PicoGreen (Invitrogen, Carlsbad, Calif.) assays, respectively.

Histology and Immunohistochemistry

Tissue rings and 3-ring tubes (N=2) were fixed in 10% neutral buffered formalin overnight, embedded in paraffin and sectioned at 5 microns. Rings were sectioned in either axial or vertical planes. Tubes were sectioned first in the axial plane and then reembedded in paraffin and sectioned in the vertical plane. Mounted tissue sections were deparaffinized and rehydrated. Safranin O (Acros Organics) was used to stain for sulfated GAG content with a Fast Green counterstain (Fisher Chemical). For immunohistochemical staining, the presence of type II collagen was detected using anticollagen type II primary antibody (abcam ab34712, Cambridge, UK) with a Fast Green counterstain. A section of the human knee articular cartilage and underlying subchondral bone served as a positive and negative control, respectively. Samples stained with isotype-matched IgG instead of primary antibody also served as negative controls. Histostain-Plus Bulk kit (Invitrogen) with aminoethyl carbazole (AEC; Invitrogen) was used to visualize the primary antibody. Images of stained tissues were acquired using an Olympus BX61VS microscope (Olympus, Center Valley, Pa.) with a Pike F-505 camera (Allied Vision Technologies, Stadtroda, Germany).

Tissue Dimension Measurements and Biomechanical Analysis

Rings

Day 21 tissue engineered rings and rat tracheal sections were sent in chondrogenic media from Case Western Reserve University to Worcester Polytechnic Institute (transit time was 3 nights and 1 night, respectively). Rings were then allowed to equilibrate for approximately 2 h in a 37° C. incubator prior to mechanical testing. Tissue ring wall thickness was measured in PBS using a machine vision system (DVT Model 630; DVT Corporation, Atlanta, Ga.). Measurements were taken in four locations around each ring using edge detection software (Framework 2.4.6; DVT), and the average thickness was used to calculate the average cross-sectional area. Each rat trachea was also measured in four locations, but using calipers due to its more uneven shape. Tissue engineered rings with and without microspheres and rat trachea sections were tested in uniaxial tension (ElectroPuls E1000 with a 50 N load cell; Instron, Norwood, Mass.) using a modified version of a system described previously. Briefly, small stainless steel pins were bent into an "L" shape and served as grips for individual rings (FIG. 11A inset). After applying a 5 mN tare load, engineered rings were pulled in tension to failure at a rate of 10 mm/min. PBS was dripped on tissues during testing to prevent drying. From this test, the maximum load the rings could withstand was calculated. The ultimate tensile stress (UTS) was calculated by dividing the failure load by the cross-sectional area. Each engineered ring was approximated as a torus and each native trachea section was approximated as a hollow cylinder.

Tubes

Tissue engineered 6-ring tubes and 8 mm sections of rat trachea were equilibrated in PBS with 0.1% protease inhibitor (Sigma-Aldrich), and their outer diameters were measured by applying a pre-load of 3 mN with an R Series Controller mechanical testing device (Test Resources Inc., Shakopee, Minn.). Individual tubes and tracheas were tested in luminal collapse as previously described with modifications. Each tube and trachea was compressed by 2 mm (luminal diameter) at a rate of 0.5 mm/min. The load was held for 6 min and then was removed at a rate of 60 mm/min. The load to collapse the lumen by 80% (1.6 mm) was used for comparison between the engineered tubes and rat tracheas. This was done to ensure that only the load required to collapse the lumen without compressing the walls of the tube was analyzed.

Tube outside diameter was measured again after a 5 min no-load period. Percent luminal recoil was calculated as the ratio of the final outer diameter/initial outer diameter*100. Video recordings (Galaxy S4 phone camera) were taken of a representative hMSC tube, hMSC þ MS tube and a section of rat trachea (after 1 freeze/thaw) compressed by a hand-held pipet to show repetitive luminal collapse and recoil of the tubes.

Statistical Analysis

One-way ANOVA with Tukey's post hoc tests were used to statistically analyze tissue engineered constructs and native tracheas via InStat 3.06 software (GraphPad Software Inc., La Jolla, Calif.). All values are reported as mean±standard deviation. Post tests were performed when $p<0.05$.

Results

Microsphere Characterization

Figure 6:
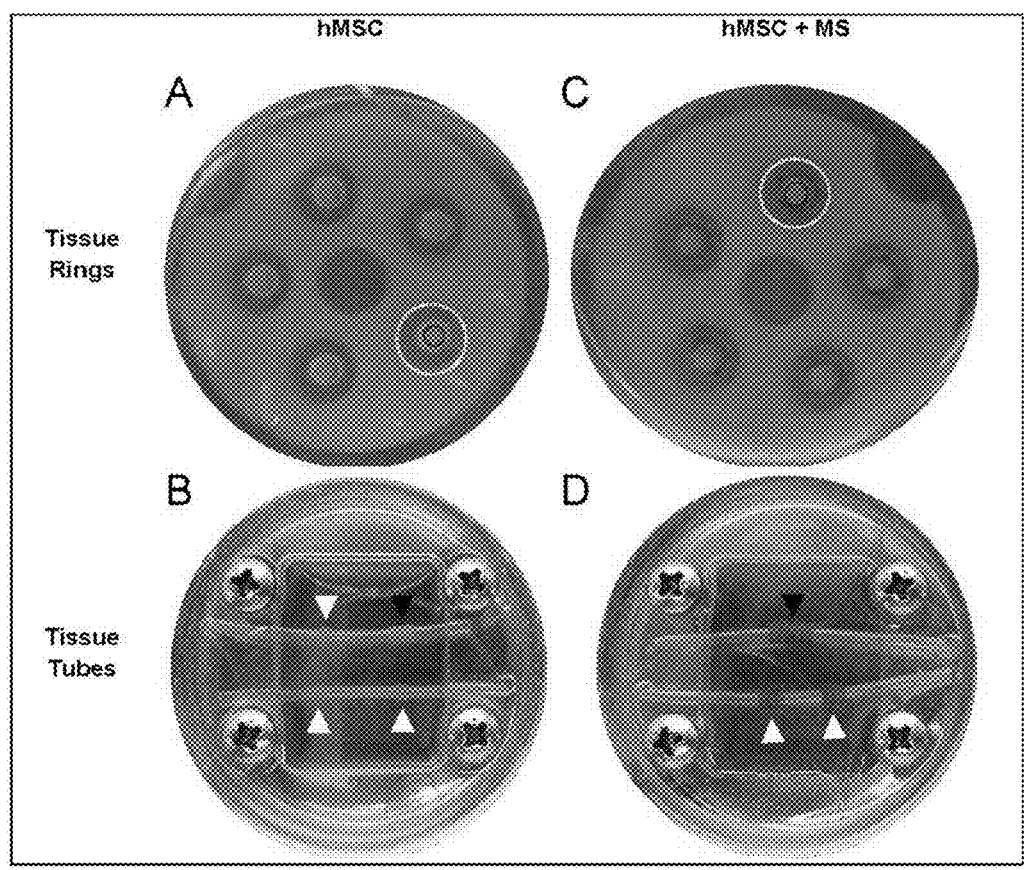
FIG. 6 illustrates macroscopic images of cartilage tissue rings and tubes in culture. Tissue rings were formed by seeding a suspension of (A) hMSCs or (C) hMSCs with microspheres in custom designed agarose annular wells (white dotted outline) with 2 mm posts (black dotted outline). (B, D) On Day 2, some of the rings were stacked on silicone tubes, which were clamped in a custom designed holder, to form 3-ring (white arrow) or 6-ring (black arrow) tissue tubes. MS=Microspheres.

Gelatin microspheres appeared blue as a result of the crosslinking reaction with genipin. They were 26.6±8.0% crosslinked, and their average diameter was 67.8±55.1 mm (N=268). A representative light microscopy image shows microspheres size variability (FIG. 5). Several hours after seeding, hMSC and hMSC+MS rings had self-assembled around the posts. After 2 days of culture, hMSC microsphere-containing rings appeared thicker and darker due to presence of microspheres compared to hMSC-only tissues, which were opaque off-white (FIGS. 6A and C). The surface of hMSC þ MS rings was less smooth compared to that of hMSC-only rings. Both hMSC-only and hMSC þ MS rings could be handled with tweezers for tissue tube assembly into 3-ring or 6-ring tubes (FIGS. 6B and D), but microsphere-containing rings held their toroid shape better during transfer from the agarose posts to the silicone tubes.

Gross Morphological Assessment

Tissues harvested after 22 days of total culture were firm and could be easily handled. The thickness of hMSC-only rings was more irregular compared to microsphere-containing rings, which were visually thicker and slightly blue due to residual microspheres that were not fully degraded (FIGS. 7A and D). Stacked rings formed fused 3-ring or 6-ring tissue tubes on the 2 mm silicone tubing (FIG. 7B-F). Rings and 3-ring tissue tubes were pink due to residual media in the tissue, while 6-ring tissue tubes and rat tracheas were rinsed in PBS before being photographed. Similar to the microsphere-containing rings, tubes with microspheres were visually thicker than hMSC-only tubes. hMSC+MS tubes were also longer than the hMSC-only tubes. Incorporation of microspheres contributed to formation of ridged surfaces on tubes compared to smooth surfaces on hMSC-only tubes. Rat tracheas had visibly thinner walls compared to tissue engineered tubes (FIG. 7G).

Biochemical Analysis

Individual rings and 3-ring tubes were analyzed biochemically. As expected, DNA (FIG. 8A), an indirect measure of cell number, and GAG (FIG. 8B) content were significantly greater in tubes compared to individual rings because 3 rings were used for each tube. There was no significant increase in GAG production per DNA (FIG. 8C) in tissues grown in ring compared to tube geometries. Addition of growth factor-delivering microspheres did not significantly affect the cell number at the time of harvest as measured by amount of DNA. However, microspheres significantly increased total GAG and GAG production per cell. GAG/DNA was greater in hMSC þ MS tissues than those without MS by factors of 2.2 and 1.7 in rings and tubes, respectively.

Histology and Immunohistochemistry

Safranin O with a Fast Green counterstain was used to visualize the presence and distribution of GAG in tissue engineered rings (FIGS. 9A and C), 3-ring tubes (FIGS. 9B and D) and rat trachea (FIG. 9E). Rings and tubes with microspheres (FIGS. 9C and D) stained more intensely for GAG compared to cell-only constructs (FIGS. 9A and B), corroborating the biochemical analysis. hMSC+MS rings and tubes were also visually thicker and had a more uniform GAG distribution with a smaller fibrous capsule (stained blue/green by Fast Green) on the tissue periphery compared to the hMSC-only tissues. The remaining gelatin microspheres that were not fully degraded by cell-secreted enzymes were visible in the hMSC þ MS groups (black arrows in FIGS. 9C and D). Cartilaginous portions of the rat trachea had the most intense GAG staining. Vertical cross sections of tissue engineered tubes of both compositions showed seamless ring fusion. hMSC-only tubes appeared to have lower GAG density in the middle of the constructs. Microsphere-containing tubes maintained ridges from the individual rings that were fused together. Cartilage rings in the rat trachea were separated by noncartilaginous fibrous tissue, which stained blue/green.

The presence and distribution of collagen type II were visualized via immunohistochemical staining (FIG. 10). hMSC and hMSC+MS rings and tubes both showed strong staining for type II collagen, which was more prevalent on the interior of the constructs. However, staining was better distributed in microsphere-containing tissues. Human knee tissue control showed appropriate collagen type II staining of articular cartilage while not staining the subchondral bone.

Tissue Dimension Measurements and Biomechanical Analysis

Rings

The walls of engineered hMSC-only and hMSC+MS cartilaginous rings were significantly thicker than those of native rat tracheas (FIG. 11A). Incorporation of microspheres resulted in rings that were significantly thicker than their cell-only counterparts. Uniaxial tension mechanical testing (FIG. 12A inset) revealed that the maximum force at failure (FIG. 12A) was similar in the engineered rings, but rat tracheal rings required a significantly smaller load to rupture. However, when force at failure was normalized to loaded area (ultimate tensile stress; FIG. 11B), microsphere-containing rings (2.44±0.22 mm² cross-sectional area) behaved similarly to the rat trachea (1.22±0.16 mmlong; 1.11±0.19 mm2 cross-sectional area), while hMSC-only rings (1.26±0.24 mm2 cross-sectional area) exhibited significantly greater stress at failure than the other two groups.

Tubes

Figure 13:
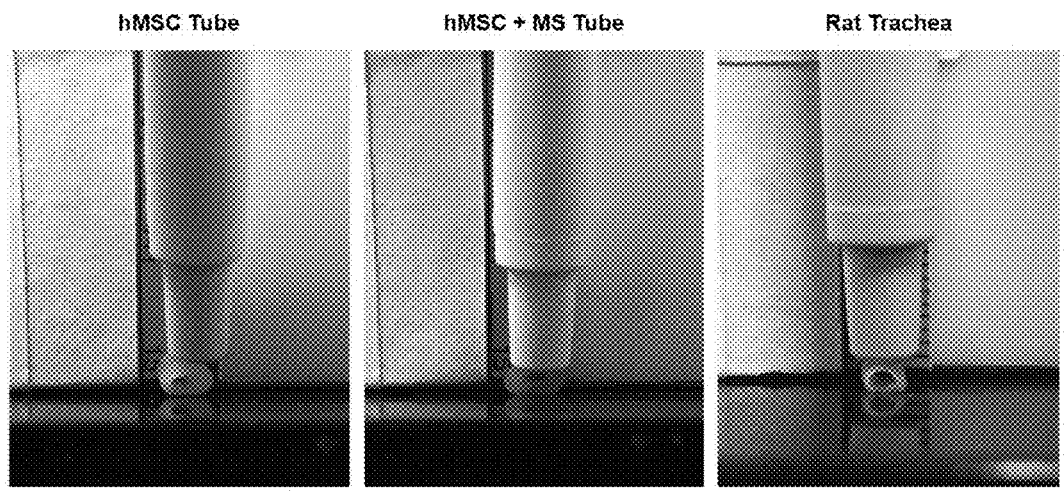
FIG. 13 is an image showing repeated manual compression and release of a representative hMSC tube, hMSC+MS Tube and a section of a rat trachea. MS=Microspheres.

Tissue engineered tubes had a significantly greater outer diameter than the rat tracheas (FIG. 11B). In addition, microspheres containing tubes had a significantly greater outer diameter than hMSC tubes. In a gross biomechanical assessment of the tissue tubes, the qualitative force required to collapse the tubes with a hand-held pipet was the largest for the hMSC þ MS tube (FIG. 13). Quantitative mechanical analysis corroborated the qualitative findings. A force was applied to collapse the tubes by 2 mm, the engineered tissues' inner diameter (FIG. 12C inset). The force required to collapse 80% of the lumen of engineered hMSC+MS tubes were about 2.1-2.3 times greater than the force required to collapse hMSC-only tubes and similarly-sized, 8 mm length sections of rat tracheas (FIG. 12C). Cell-only tubes required approximately the same load to achieve luminal collapse compared to the hMSC+MS tubes. After the load was removed, the outer diameters of the tubes were measured again and it was found that all tubes recoiled to nearly 100% of their original diameters (FIG. 12D).

This Example demonstrates the ability to form cartilaginous rings from human bone marrow-derived MSCs in custom culture wells and stack the rings to generate fused tissue tubes. Secondly, this work shows that incorporation of microspheres delivering chondrogenic growth factor (i.e., TGFβ1) into the self-assembled ring- and tube-shaped constructs would enhance neocartilage formation by increasing matrix production, tissue dimensions and mechanical properties. Custom annular culture wells comprised of agarose were used to successfully engineer hMSC-only and microsphere containing rings. On day 2 of culture, rings could be manipulated and stacked onto a silicone tube to fuse into tissue tubes. The two days of culture needed in this study is a much shorter time than the previously reported 3-4 week culture period necessary for high-cell density chondrocyte sheets to achieve mechanical integrity required for manual manipulation. After approximately 3 weeks of culture, tubes were easily removed from the silicone support and exhibited seamless fusion between rings as observed via gross morphological and histological evaluation (FIGS. 7, 9 and 10). The homogenous fusion between 2-day-old high-density hMSC-derived cartilage rings are consistent with the previously reported fusion of high density hMSC pellets undergoing chondrogenesis. The presence of GAG (FIGS. 8 and 9) and collagen II (FIG. 10) indicated cartilaginous tissue formation after 22 days of total culture. These findings confirmed that custom agarose molds can be used to engineer cartilaginous rings and that these rings can be fused into tissue tubes.

While there are reports describing fabrication of rabbit auricular chondrocyte-derived cartilage sheets that were rolled to fuse into a tube in vitro or in vivo, our approach has advantages over these systems. First of all, human bone marrow MSCs used here as the cell source for autologous cartilage tissue formation avoids the need for invasive and potentially detrimental harvest of mature cartilage tissues and provides the capacity for cell expansion to achieve necessary numbers of cells capable of undergoing chondrogenesis. In addition, the use of human cells in our system is potentially a more translatable strategy, as approaches utilizing cells from different species may result in different chondrogenic outcomes compared to those with human cells, delaying or inhibiting transfer of technology to the clinical setting. Secondly, the hMSC-based cartilaginous rings were significantly thicker than previously reported chondrocyte-based approaches. In just 3 weeks of culture, hMSC derived cartilage rings were 0.89 mm (hMSC-only) and 1.25 mm (hMSC+MS) thick compared to rabbit articular chondrocytederived cartilage, which was 235 mm thick after 8 weeks of culture, and rabbit auricular chondrocyte-derived cartilage, which was about 500 mm thick after 6 weeks of culture and 553 mm thick after 8 weeks of culture. To achieve wall thicknesses similar to those found in our hMSC-based rings, multiple cartilage sheets would need to be stacked or folded. Thirdly, in terms of cartilage tube fabrication, the ring assembly system does not require the binding of tissue sheets with sutures or ties to form a tubular construct. More importantly, our ring-based approach is a modular system which could prove advantageous when generating multi-tissue type constructs because each ring could serve as a tissue building block. Finally, the ring-to-tube technology may be more favorable in resisting compression in the axial plane, thereby maintaining tracheal patency in future in vivo applications, compared to sheet-to-tube technologies which may have heterogeneous mechanical properties around the circumference of the tube. While rat hepatocyte cell line rings and 2-ring tubes, normal human fibroblast rings and smooth muscle cell rings and tubes have been reported, the fabrication of scaffold-free, stem cell based cartilage-like rings and tubes using a custom ring and tube assembly system has not yet been demonstrated.

The degree of chondrogenesis was also compared between tissues developed from high-density hMSC ring and tube cultures containing proteolytically-degradable TGF-β1-loaded gelatin microspheres and hMSC-only tissues grown in the same geometries with exogenously delivered growth factor. This high-cell density culture system with bioactive microspheres has previously been shown to enhance chondrogenesis, mechanical properties and/or tissue thickness in hMSC-derived aggregate and sheet constructs. In the present work, tissues with bioactive microsphere were visually thicker (both rings and tubes) and longer (tubes) than hMSC-only constructs. Tubes created from microsphere containing rings maintained outer ridge morphology reminiscent of the rings used for fusion (FIGS. 7E, F and 9D). It is possible that even after only 2 days of culture, incorporation of TGF-β1-loaded microspheres encouraged greater and/or more mature matrix deposition in tissue rings, making the remodeling of ECM more challenging during the fusion process. Another possible reason for the presence of ridges in the hMSC+MS tubes is that incorporation of microspheres led to a more uniform cartilaginous matrix distribution and a reduced fibrous capsule, which has been reported to encourage cartilage tissue fusion. This GAG-poor capsule, sometimes seen on the periphery of high-cell density cultures, was more prevalent in hMSC-only tissues and may be the reason for smoother surfaces found in hMSC-only tubes (FIGS. 9A and B) compared to the GAG-rich, ribbed hMSC+MS tubes (FIGS. 9C and D).

Incorporation of growth factor-loaded microspheres enhanced chondrogenesis as detected by biochemical and histological assays and measurement of tissue dimensions. This finding is corroborated by previous reports of improved cartilage formation in high-density hMSC systems with incorporated TGF-b1-loaded gelatin microspheres. Compared to hMSC-only rings and tubes, hMSC+MS rings and tubes produced more GAG per DNA (FIG. 8C) and stained more intensely for GAG (FIG. 9) and collagen type II (FIG. 10), which are all indicative of neocartilage formation. Not only was the ECM more cartilaginous, addition of growth factor loaded microspheres led to increased tissue ring thickness and tube outer diameter (FIG. 11). Taken all together, the biochemical, histological and tissue dimension data supported our hypothesis that incorporation of growth-factor-loaded microspheres into the hMSC high-cell density rings and tubes improved chondrogenesis in the constructs.

Upon mechanical evaluation of tissue engineered rings and tubes, incorporation of microspheres decreased ring tensile strength and did not affect tubular luminal elasticity. Uniaxial UTS values showed that incorporation of microspheres resulted in a lower stress at failure (FIG. 12B). Even though the load at failure was only slightly lower in hMSC+MS rings than hMSC-only rings (no significant difference; FIG. 12A), the hMSC+MS rings had a significantly greater cross-sectional area (FIG. 11A) resulting in a significantly smaller UTS. Still, reduced UTS values were an unexpected finding since incorporation of growth factor-laden microspheres has been shown to increase the equilibrium compressive moduli of hMSC-derived engineered cartilage sheets. However, the residual gelatin microspheres that were not fully degraded could have been acting as inclusions, thereby weakening the tissues' tensile strength. Another potential explanation for decreased UTS is the differences in biochemical make-up of the ECM in the hMSC+MS compared to hMSC-only rings. The GAG content is a dominant contributor to increased tissue stiffness in compression and collagen content is predominantly responsible for tensile properties in cartilage tissues. While the addition of microspheres significantly increased GAG biochemical content as well as GAG and type II collagen staining, it is possible that microspheres led to a greater relative increase in GAG compared to collagen resulting in lower tensile properties in the hMSC+MS rings than the hMSC-only rings. Mechanical evaluation of tissue tubes showed that all tissue tubes recoiled to almost the original outer diameter, but microsphere-containing tissues required greater force to collapse the tubes. However, microsphere containing tubes were also qualitatively longer than their cell-only counterparts so it is difficult to examine the role that microspheres played on the luminal elasticity mechanics of the tissue tubes.

Tissue generation was influenced by culture in the custom wells and assembly system in the ring and tube geometries. Three-ring tubes had significantly greater DNA and GAG content than individual rings, although these increases were slightly less than the 3-fold proportional increases that would be expected. However, GAG production per cell was not significantly different between ring and tube geometries. Unexpectedly, with and without microspheres, both geometries led to approximately two-fold greater GAG/DNA production compared to high-cell density sheets grown on cell culture inserts using same passage hMSCs from the same donor as used. It is possible that the agarose culture wells limited the diffusion of ECM molecules produced by cells into the bulk medium, thereby increasing their effective concentration in the constructs and the probability of macromolecule assembly and matrix maturation. For example, aggrecan, a cartilage-specific proteoglycan which plays an important role in resisting cartilage compression during loading, is noncovalently bound to hyaluronic acid and stabilized by link protein to form large aggrecan aggregates outside the cell. Collagen fiber bundles are also assembled extracellularly. Additionally, proteoglycane collagen interaction is essential for cartilaginous ECM function. A potentially similar biophysical approach called macromolecular crowding, which incorporates large molecules as a means of increasing medium density and limiting diffusion, has been shown to drastically increase deposition of type I collagen by fibroblasts in tissue culture. Another possibility for improved chondrogenesis is the increased surface area to volume ratio of the toroid compared to sheet culture for the same number of cells, which could result in greater availability of oxygen and nutrients and better removal of waste via diffusion.

The custom well and assembly system in this Example was used to engineer a tracheal replacement which can be initially tested in a small animal model for tracheal defects in a rat. With regard to tissue dimensions, rat tracheas have a similar lumen diameter but the walls of engineered rings were significantly thicker (FIG. 11A) and tubes had significantly greater outer diameters (FIG. 11B) compared to rat tracheas. Mechanical evaluation by uniaxial UTS on the rings and luminal collapse and recoil on the tubes showed that scaffold-free cartilaginous rings and tubes perform at least as well as native rat trachea, suggesting that these engineered tissues may be able to provide the mechanical rigidity necessary to maintain airway patency in the rat. It is promising that the tissue engineered microsphere-containing neocartilaginous tubes required significantly greater loads to collapse the lumen compared to the similarly-sized rat tracheal segments because a trachea for clinical use in humans will likely need to be stiffer than a rat trachea. While tissue engineered cartilage rings and tubes appeared thicker than rat tracheal cartilage, they are very similar to the thickness of human tracheal cartilage rings. Unlike the tissue engineered torus rings with a circular cross-section presented here, human tracheal cartilage rings are toroid-like with a more rectangular-shaped cross-sectional area which is typically about 1 mm radially and about 4 mm vertically. Control over the vertical dimension of engineered tubes can be achieved by fusing multiple rings together, as shown in this Example. A longer engineered trachea would simply require more cells, microspheres, growth factor and media, but tissue generation should not be inhibited by the length of the construct. Adult human trachea also has a much larger lumen, measuring at least 12 mm in diameter, but using this approach it will be possible to engineer larger diameter rings and tubes by modifying the size of the cell culture annular wells for ring self-assembly and the support strut for tube culture. Additionally, the geometry of the culture-wells and the tissue assembly approach can be easily altered to produce self-assembled tissues of specific shapes (e.g., oval tissues with defined wall thickness, cone like structures, or even figure-eight, honeycomb and dog bone shaped constructs) for applications necessitating geometrical control over anatomical features and/or tissue-level morphology.

A functional tracheal replacement may require much more complexity in tissue organization and function. While the cartilaginous portion of the native trachea provides support to the airway, intervening vascularized fibrous tissue is necessary to supply the cartilaginous rings and mucosal and submucosal layers lining the tracheal lumen with nutrients and oxygen. Our customizable tissue assembly system may permit the integration of these vital tissue components to replicate actual tracheal architecture and ultimately function. Firstly, donor-specific needs with regard to tissue anatomy may be addressed by employing annular wells and support struts with custom geometry to engineer the organ. Next, different cell sources and/or differentiation conditions for the tissue units can be used to engineer tissues with requisite properties, such as rings with neovasculogenic capabilities or tubes of tracheal epithelium. Thirdly, incorporation of bioactive microspheres with different compositions into each type of tissue ring may allow for spatial as well as temporal control of cell differentiation and neotissue formation even after multi-tissue fusion. It is also possible that incorporation of growth factor-loaded microspheres can decrease in vitro culture time by releasing bioactive factors after implantation, and in doing so stimulate in vivo tissue maturation and physiological healing. The use of bioactive microspheres in the modular custom culture system described here is a promising approach for tracheal tissue regeneration.

Example 2

This Example shows the generation of osteognic rings and tubes from hMSC that include TGF-β1 and BMP-2 loaded nanoparticles.

hMSC Isolation and Expansion

Human mesenchymal stem cells (hMSCs) were isolated from the posterior iliac crest of 3 healthy male donors (43±5 years) using a protocol approved by the University Hospitals of Cleveland Institutional Review Board and cultured as previously described. Briefly, the aspirates were rinsed with low-glucose Dulbecco's modified Eagle's medium (DMEM-LG; Sigma-Aldrich, St. Louis, Mo.) with 10% prescreened fetal bovine serum (Sigma-Aldrich). Mononucleated cells were isolated using a Percoll (Sigma-Aldrich) density gradient then plated on tissue culture plastic at a density of $1.8 \times 10^5$ cells per $cm^2$ in medium containing 10 ng/ml fibroblast growth factor-2 (FGF-2; R&D Systems, Minneapolis, Minn.) and cultured at 37° C. with 5% $CO_2$. Nonadherent cells were removed after 4 days. The adherent cells, primary hMSCs, were cultured for another 10-14 days with media changes every 3 days. They were then reseeded at $4 \times 10^3$ cells/$cm^2$ and expanded until passage 2, when they were stored in liquid nitrogen in DMEM-LG with 10% dimethyl sulfoxide (DMSO) until use.

Gelatin Microsphere (GM) Synthesis and TGF-β1 Loading

Gelatin microspheres (GM) were synthesized using a water-in-oil single emulsion technique and crosslinked with genipin for 2 hours as previously described. Briefly, 11.1% w/v acidic gelatin (Sigma-Aldrich) was dissolved in deionized water (diH$_2$O), added drop-wise into 250 ml preheated (45° C.) olive oil (GiaRussa, Coitsville, Ohio) and magnetically stirred at 500 RPM. After 10 minutes, stirring ensued at 4° C. for 30 minutes. 100 ml acetone chilled at 4° C. was added to the emulsion and again an hour later. Stirring rate increased to 1000 RPM for 5 minutes after which the solution was filtered and the resulting microspheres were washed with acetone and dried overnight. Microspheres were then crosslinked with 1% w/v genipin (Wako USA, Richmond, Va.) on a magnetic stir plate at RT. After 2 hours, the crosslinked microspheres were rinsed 3 times with diH$_2$O and lyophilized. Characterization of GM can be found in Solorio et al. 2012. Prior to adding the microparticles to the hMSC suspension, empty GM were incubated with PBS for 2 hours at 37° C. For exogenous growth factor supplementation, TGF-β1 (Peprotech, Rocky Hill, N.J.) was added to the medium at 10 ng/ml.

Mineral-Coated Hydroxyapatite Microparticle (MCM) Synthesis and BMP-2 Loading

Hydroxyapatite (HA) microparticles ranging from 3-5 μm in diameter from Plasma Biotal LTD (Derbyshire, UK) were mineral-coated in modified simulated body fluid (mSBF) and loaded with BMP-2 as previously described. Briefly, HA microparticles were added at 2 mg/ml to mSBF (pH 6.8) containing 141 mM NaCl, 4.0 mM KCl, 0.5 mM MgSO$_4$, 1.0 mM MgCl$_2$, 20.0 mM HEPES, 5.0 mM CaCl$_2$, 2.0 mM KH$_2$PO$_4$ and 4.2 mM NaHCO$_3$ (all from Fisher Scientific) The solution was stirred continuously at 37° C. for 7 days with the mSBF refreshed daily. At the end of the coating process, the MCMs were rinsed with diH$_2$O and lyophilized. Prior to adding the microparticles to the hMSC suspension, empty MCM were incubated with PBS for 4 hours at 37° C. For exogenous growth factor supplementation, BMP-2 (Dr. Walter Sebald, Department of Developmental Biology, University of Würzburg, Germany) was added to the medium at 100 ng/ml.

Cell Culture Well Preparation

Agarose molds for cell culture were prepared as previously described. Briefly, a polycarbonate sheet (Small Parts Inc., Miramar, Fla.) was machined to contain annular wells with concentric 2 mm diameter posts surrounded by a 3.75 mm wide trough. A polydimethylsiloxane (PDMS; Sylgard 184, Dow Corning) negative mold of the polycarbonate template was cured and sterilized. Two percent w/v agarose (Denville Scientific Inc., Metuchen, N.J.) in DMEM-LG (Sigma-Aldrich) was autoclaved and used to fill the PDMS mold. After cooling, the ring-shaped culture wells were removed from the PDMS mold, moved into 6-well plates (BD Falcon), and incubated overnight in a serum-free, chemically-defined basal pellet medium (BPM) containing DMEM-HG (Sigma-Aldrich) with 10% ITS+Premix (Corning), 1 mM sodium pyruvate (HyClone), 100 µM non-essential amino acids (Lonza), 100 nM dexamethasone (MP Biomedicals, Solon, Ohio), and 0.05 mM L-ascorbic acid-2-phosphate (Wako).

Assembly of Microsphere-Containing Tissue Rings and Tubes

Trypsinized hMSCs (400,000 cells) with or without 0.3 mg GM and 0.08 mg MCM in 50 µL media were seeded in a circular fashion in each custom designed annular well and cultured in BPM+10 ng/ml TGF-β1. After 24 hours, agarose wells were flooded with media. On day 2, the self-assembled rings were transferred from the annular wells onto 2-mm glass tubes (Adams & Chittenden Scientific Glass, Berkeley, Calif.) as individual 2-mm rings, or to form 3×2-mm and 8×2-mm tubes. Glass tubes were placed on top of custom engineered polycarbonate holders and tissue rings/tubes were cultured horizontally in 60 mm petri dishes (BD Falcon) in a humidified cell culture incubator at 37° C. and 5% $CO_2$ for 2 weeks in chondrogenic induction medium (BPM+10 ng/ml TGF-β1) followed by 3 weeks in osteogenic induction medium comprised of DMEM-HG (Sigma-Aldrich) with 10% ITS+Premix (Corning), 1 mM sodium pyruvate (HyClone), 100 µM non-essential amino acids (Lonza), 100 nM dexamethasone (MP Biomedicals, Solon, Ohio), 0.173 mM L-ascorbic acid-2-phosphate (Wako), and 5 mM β-glycerophosphate (Sigma-Aldrich)+100 ng/ml BMP-2. The induction media were changed every 3 days.

Gross Morphological Assessment

After 5 weeks, rings and tubes were harvested and gross images of all tissues were taken. Thickness and length measurements were performed using micro calipers (Fowler). Four measurements were obtained per specimen at the 12, 3, 6, and 9 o'clock positions.

Statistical Analysis

All data are expressed as mean±SD. The unpaired Student's t test was used to test for significant effects with $p<0.05$ considered significant. Data were analyzed using GraphPad Prism 6.0 software (GraphPad Software Inc., La Jolla, Calif.).

Results

Morphological Assessment

Figure 14:
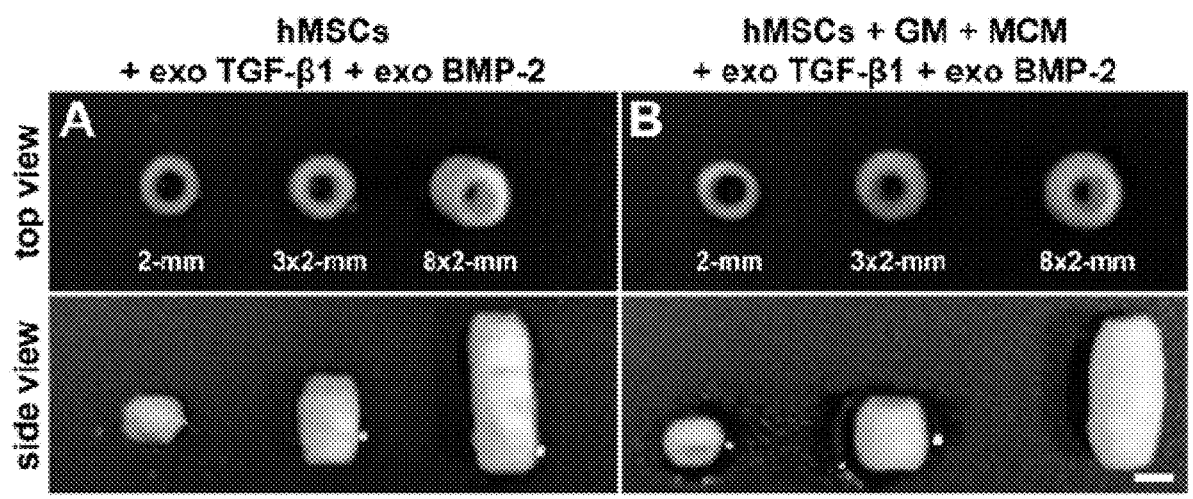
FIG. 14 illustrates images showing gross morphology of hMSC rings and tubes. Representative rings (2-mm) and tubes (3×2-mm and 8×2-mm) of A) hMSCs alone or B) hMSCs+GM+MCM cultured for 5 weeks in chondrogenic+exogenous TGF-β1 (2 weeks; 10 ng/ml) and osteogenic+BMP-2 (3 weeks; 100 ng/ml) induction media. Scale bar=2 mm.

The gross morphology of the rings and tubes was visually assessed after 5 weeks of chondrogenic and osteogenic induction in presence of TGF-β1 (2 weeks) and BMP-2 (3 weeks). Tissue rings and tubes comprised of hMSCs only were noticeably thinner compared to hMSC+GM+MCM specimens. In contrast, the overall length of the hMSC+GM+MCM rings and 3×2-mm tubes appeared reduced, while the 8×2-mm tubes had comparable lengths across groups (FIG. 14).

Figure 15:
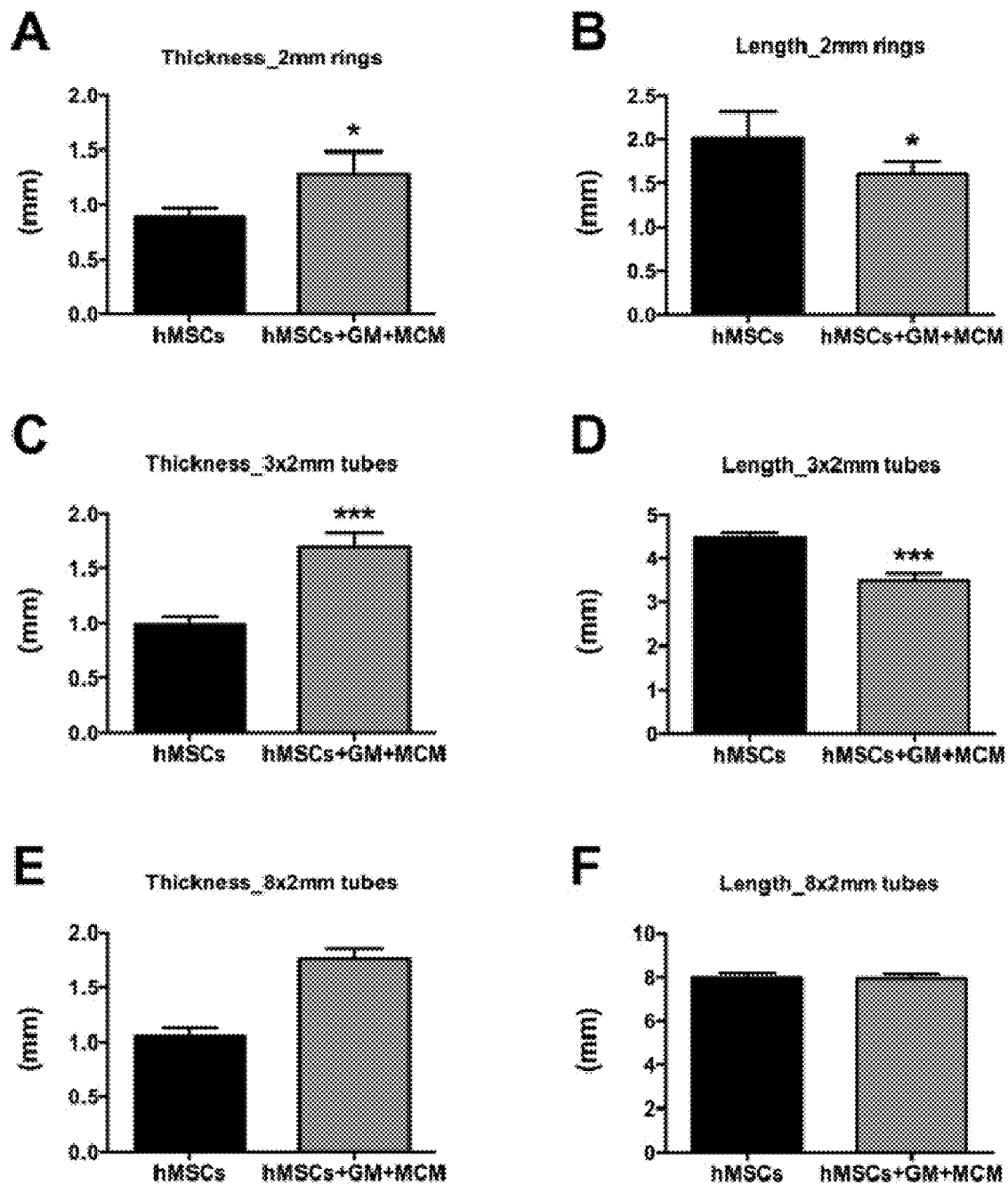
FIG. 15 illustrates graphs showing the thickness and length analyses of hMSC osteogenic or bone rings and tubes generated using the methods described herein. A,B) 2-mm rings (N=4), C,D) 3×2-mm tubes (N=2), E,F) 8×2-mm tubes (N=1). hMSCs alone or hMSCs+GM+MCM cultured for 5 weeks in chondrogenic+exogenous TGF-β1 (2 weeks; 10 ng/ml) and osteogenic+BMP-2 (3 weeks; 100 ng/ml) induction media.

Quantitative thickness and length analyses of the rings and tubes were in agreement with the qualitative assessment. Rings containing GM+MCM were significantly thicker than hMSC rings alone (FIG. 15A; $p<0.05$). Both tissue tubes (3×2-mm and 8×2-mm) revealed similar trends (FIG. 15C, E; $p<0.001$). In contrast, measurements of the hMSC+GM+MCM rings showed a significant length reduction (FIG. 15B; $p<0.05$) compared to the hMSC rings alone, which was confirmed by the 3×2-mm tubes (FIG. 15D; $p<0.001$). No differences were observed in the length of 8×2-mm tubes across groups (FIG. 15F).

Example 3

This Example shows the generation of vascular rings and tubes from smooth muscle cells that include TGF-β1 loaded microparticles.

Figure 16:
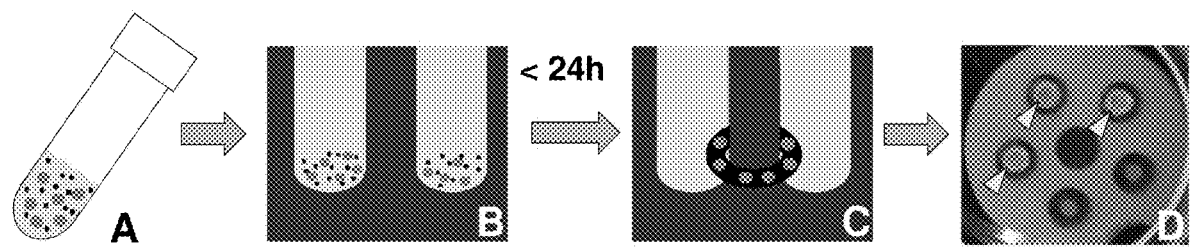
FIG. 16 illustrates a schematic view of microsphere incorporation within self-assembled vascular cell rings. A, Cross-linked gelatin microspheres were mixed in suspension with smooth muscle cells at 0, 0.2 or 0.6 mg microspheres per million cells. B, cells and microspheres were seeded into agarose molds. Cells aggregate to form self-assembled tissue rings with incorporated microspheres (C). D, Photograph of an agarose mold with three aggregated cell-microsphere rings cultured for 14 days. Arrowheads point to self-assembled tissue rings on agarose posts (2 mm post diameter).

FIG. 16 illustrates a schematic view of microsphere incorporation within self-assembled cell rings. A, Cross-linked gelatin microspheres were mixed in suspension with smooth muscle cells at 0, 0.2 or 0.6 mg microspheres per million cells. B, cells and microspheres were seeded into agarose molds. Cells aggregate to form self-assembled tissue rings with incorporated microspheres (C). D, Photograph of an agarose mold with three aggregated cell-microsphere rings cultured for 14 days. Arrowheads point to self-assembled tissue rings on agarose posts (2 mm post diameter).

Figure 17:
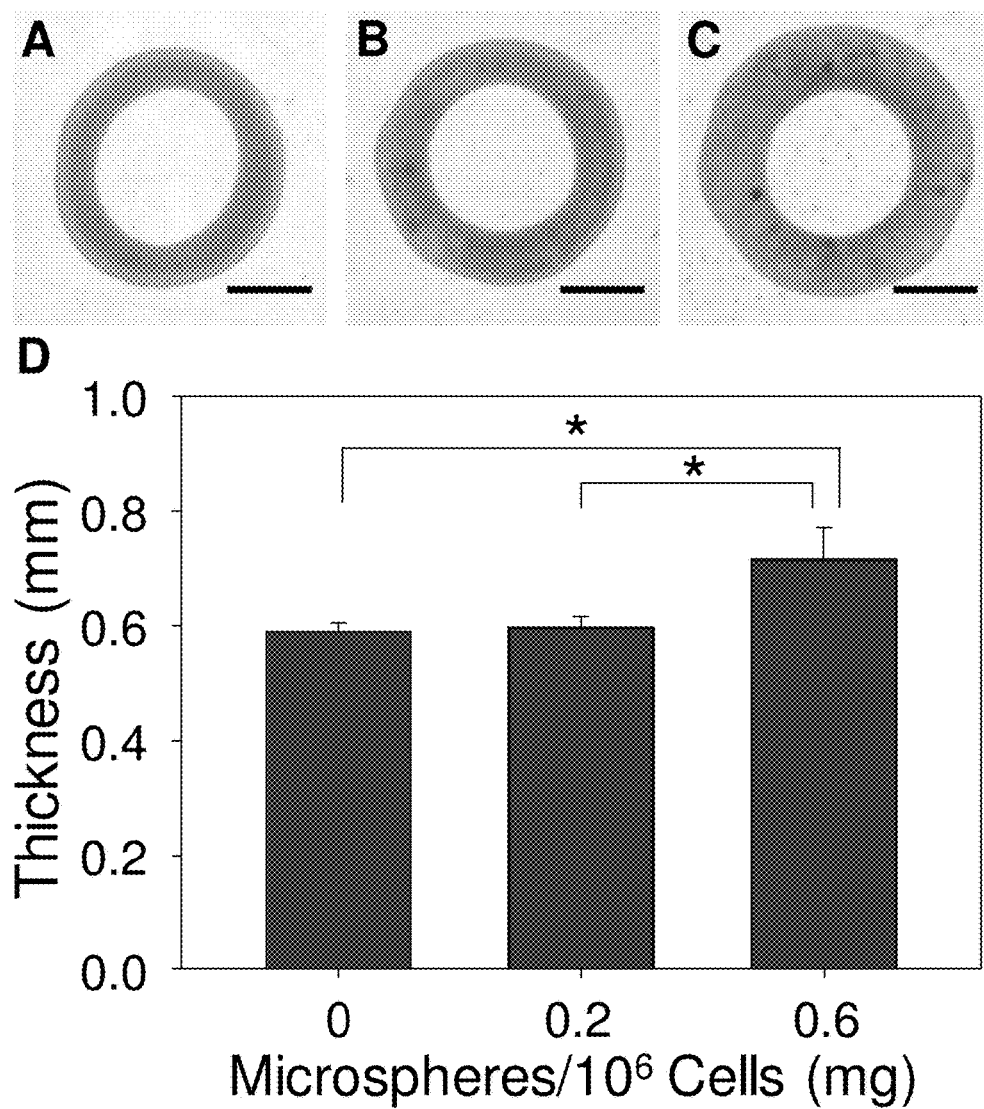
FIG. 17 illustrates images and a graph showing microspheres increased tissue ring thickness. Images of self-assembled vascular rings seeded with 0 (A), 0.2 (B), or 0.6 mg (C) of microspheres per million cells and cultured in smooth muscle growth medium for 14 days. (D) Average wall thicknesses of 14-day-old tissue rings with 0, 0.2, or 0.6 mg microspheres per million cells. Scale=1 mm, n=6, *$p<0.05$.

FIG. 17 illustrates images and a graph showing microspheres increased tissue ring thickness. Images of self-assembled cell rings seeded with 0 (A), 0.2 (B), or 0.6 mg (C) of microspheres per million cells and cultured in smooth muscle growth medium for 14 days. (D) Average wall thicknesses of 14-day-old tissue rings with 0, 0.2, or 0.6 mg microspheres per million cells. Scale=1 mm, n=6, *$p<0.05$.

FIG. 18 illustrates images showing gelatin microsphere incorporation and degradation within tissue rings. Tissue rings were seeded with 0, 0.2, or 0.6 mg microspheres per million cells, collected at 7 or 14 days, and stained with Hematoxylin and Eosin (A-F) and Picrosirius Red/Fast Green stain. Scale=100 µm.

FIG. 19 illustrates graphs showing Mechanical properties of tissue rings loaded with gelatin microspheres. Self-assembled cell rings were cultured for 14 days in growth medium and pulled to failure. Mean values for ultimate tensile strength (UTS; A), maximum tangent modulus (MTM; B), failure load (C) and failure strain (D) were calculated from stress-strain curves for each ring sample group. n=6, *$p<0.05$.

FIG. 20 illustrates an image and graph showing microspheres increased ring thickness in tissues cultured in smooth muscle differentiation medium. Rings were seeded with 0 (A), 0.2 (B), or 0.6 mg (C) of microspheres per million cells and cultured to 14 days. Rings were seeded in growth medium and switched to differentiation medium on day 1. (D) Average wall thicknesses of 14-day-old tissue rings with 0, 0.2, or 0.6 mg microspheres per million cells. Scale=1 mm; n=8 for 0 mg; n=9 for 0.2 and 0.6 mg/million cells; *$p<0.05$.

FIG. 21 illustrates images showing microsphere incorporation within tissue rings cultured in smooth muscle differentiation medium. Tissue rings were seeded in growth medium with 0, 0.2, or 0.6 mg microspheres per million cells, and switched to differentiation medium at day 1. Tissue rings were collected at 7 or 14 days, and stained with Hematoxylin and Eosin (A-F) and Picrosirius Red/Fast Green stain. Scale=100 µm.

FIG. 22 illustrates graphs showing the mechanical properties of tissue rings cultured in differentiation medium with microsphere incorporation. Self-assembled cell rings were seeded in growth medium, switched to differentiation medium on day 1, and cultured for 13 days in differentiation medium and harvested for mechanical tests (14 days total culture). Mean values for ultimate tensile strength (UTS; A), maximum tangent modulus (MTM; B), failure load (C) and failure strain (D) were calculated from stress-strain curves for each ring sample group. n=6, *$p<0.05$.

FIG. 23 illustrates images and a graph showing exogenous or microsphere-mediated TGF-β1 delivery to self-assembled tissue rings. Rings were seeded in growth medium, and switched to differentiation medium at day 1. (A) Untreated control rings with no microspheres (n=6). (B) Tissue rings treated with 10 ng/ml soluble TGF-β1 (n=8). (C,D) Tissue rings with unloaded gelatin microspheres (0.6 mg/million cells; n=6) untreated (C) or treated (D) with 10 ng/ml exogenous TGF-β1 (n=8). (E) Tissue rings with microspheres pre-loaded with TGF-β1 (400 ng TGF-β1/mg microspheres), but no exogenous TGF-β1 in the medium (n=7). Tissue rings contracted after they were removed from agarose posts, resulting in a greater decrease in diameter (F) and greater thickness (G) in rings exposed to TGF-β1. Scale=1 mm, *p<0.05.

FIG. 24 illustrates images showing hematoxylin and eosin stain (A-E) at 14 days shows microsphere degradation primarily in the groups with added TGF-β1. Collagen deposition (F-J, Picrosirius Red/Fast Green stain, red=collagen green=counterstain) in TGF-β1 groups is primarily seen around ring edges. (A,F) Control (untreated) rings. (B,G) Rings cultured with exogenous 10 ng/ml TGF-β1 added to the medium. Rings with unloaded microspheres (0.6 mg per million cells) untreated (C,H) or treated with 10 ng/ml exogenous TGF-β1 (D,I). Rings with TGF-β1 loaded microspheres (0.6 mg microspheres per million cells) and no exogenous TGF-β1 treatment (E, J). Scale=100 μm.

FIG. 25 illustrates images showing Contractile protein expression in tissue rings treated with TGF-β1. Rings were grown with either no microspheres or exogenous TGF-β1 (A,F), no microspheres but treated with 10 ng/ml exogenous TGF-β1 (B,G), with microspheres and no exogenous TGF-β1 (C,H), with unloaded microspheres and exogenous TGF-β1 (D,I) or with TGF-β1 loaded microspheres and no exogenous TGF-β1 in the medium (E,J). Rings were stained for either smooth muscle alpha actin (A-E) or calponin (F-J). Nuclei are shown in blue (Hoechst). Scale=100 μm.

FIG. 26 illustrates graphs showing the mechanical properties of tissue rings treated with TGF-β1 after 14 days in culture. Rings were cultured in differentiation medium with no microspheres or exogenous TGF-β1, no microspheres with 10 ng/ml exogenous TGF-β1, unloaded microspheres with no exogenous TGF-β1, unloaded microspheres with 10 ng/ml exogenous TGF-β1, or loaded microspheres (400 ng TGF-β1/mg microspheres) and no exogenous TGF-β1. Rings in the group with no microspheres and exogenous TGF-β1 had significantly higher ultimate tensile stresses than the loaded microsphere group (A), and the unloaded microspheres without TGF-β1 group had significantly higher failure loads than rings without microspheres or TGF-β1 (B). There were no significant differences in MTM (C) or failure strain (D). *p<0.05.

From the above description of the invention, those skilled in the art will perceive improvements, changes and modifications. Such improvements, changes, and modifications are within the skill of the art and are intended to be covered by the appended claims. All patents and publications identified herein are incorporated by reference in their entirety.

Having described the invention, we claim:

1. A method of forming a modular engineered tissue construct, the method comprising:
    providing a plurality of ring-shaped, self-assembled, scaffold-free, high-density cell aggregates, at least one cell aggregate including a plurality of cells and a plurality of biocompatible and biodegradable nanoparticles and/or microparticles that are incorporated within the cell aggregates, wherein at least one of the plurality of ring-shaped, self-assembled, scaffold-free, high-density cell aggregates is formed by:
        culturing a suspension of nanoparticles and/or microparticles and undifferentiated and/or substantially differentiated progenitor cells in an annular well to form a ring-shaped, self-assembled, scaffold-free, high-density cell aggregate; and
        removing the ring-shaped, self-assembled, scaffold-free, high-density cell aggregate;
    the nanoparticles and/or microparticles acting as a bulking agent within the cell aggregate to increase the cell aggregate size and/or thickness and improve the mechanical properties of the cell aggregate; and
    the nanoparticles and/or microparticles including at least one bioactive agent for delivery of the at least one bioactive agent wherein the at least one bioactive agent is differentially and/or controllably released by the nanoparticles and/or microparticles;
    stacking the plurality of ring-shaped, self-assembled, scaffold-free, high-density cell aggregates on a support; and
    culturing the stacked ring-shaped, self-assembled, scaffold-free, high-density cell aggregates on the solid support in a culture medium to fuse the aggregates and promote tissue formation.

2. The method of claim 1, wherein the at least one of the plurality of ring-shaped, self-assembled, scaffold-free, high-density cell aggregates is formed by:
    providing undifferentiated and/or substantially differentiated progenitor cells;
    combining the undifferentiated and/or substantially differentiated progenitor cells with a plurality of nanoparticles and/or microparticles so that the nanoparticles and/or microparticles are dispersed and suspended with the undifferentiated and/or substantially differentiated progenitor cells in a culture medium; and
    culturing the suspension of nanoparticles and/or microparticles and undifferentiated and/or substantially differentiated progenitor cells in an annular well to form a ring-shaped, self-assembled, scaffold-free, high-density cell aggregate.

SEQUENCE LISTING

<160> NUMBER OF SEQ ID NOS: 1

<210> SEQ ID NO 1
<211> LENGTH: 6
<212> TYPE: PRT
<213> ORGANISM: Homo sapiens

<400> SEQUENCE: 1

Gly Arg Gly Asp Ser Pro
1               5

3. The method of claim 1, wherein the plurality of ring-shaped, self-assembled, scaffold-free, high-density cell aggregates comprise differing aggregate materials to form a heterogeneous tissue construct, at least one of the ring-shaped, self-assembled, scaffold-free, high-density cell aggregates being provided or formed with or without nanoparticles and/or microparticles and having different properties than the other aggregates to vary the properties of the construct for particular tissue engineering application.

4. The method of claim 1, wherein the at least one of the fused self-assembled, scaffold-free, high-density cell aggregates comprises a plurality of chondrogenic cells.

5. The method of claim 3, wherein the stacked, ring-shaped, self-assembled, scaffold-free, high-density cell aggregates includes alternating first engineered ring-shaped, self-assembled, scaffold-free, high-density cell aggregates and second engineered ring-shaped, self-assembled, scaffold-free, high-density cell aggregates, wherein the first and second engineered stacked ring-shaped, self-assembled, scaffold-free, high-density cell aggregates form heterogeneous tubular shaped construct.

6. The method of claim 5, wherein the first engineered ring-shaped, self-assembled, scaffold-free, high-density cell aggregates define cartilaginous portions within the tubular shaped construct and the second engineered ring-shaped, self-assembled, scaffold-free, high-density cell aggregates define noncartilaginous portions within the tubular shaped construct, wherein the first and second engineered stacked ring-shaped, self-assembled, scaffold-free, high-density cell aggregates are arranged end-to-end in an alternating manner.

7. The method of claim 1, the nanoparticles and/or microparticles comprising a biocompatible and biodegradable polymer.

8. The method of claim 1, bioactive agent including at least one of TGF-β1 and/or BMP-2.

9. The method of claim 5, the plurality of cells in the first engineered ring-shaped, self-assembled, scaffold-free, high-density cell aggregates consisting of a plurality of chondrogenic cells and the plurality of cells in the second engineered ring-shaped, self-assembled, scaffold-free, high-density cell aggregates consisting of non-chondrogenic cells.

10. The cells according to claim 9, the chondrogenic cells selected from the group consisting of mesenchymal stem cells.

11. The cells according to claim 9, the non-chondrogenic cells being vascular progenitor cells selected from the group consisting of human umbilical vein endothelial cells and/or smooth muscle cells.

12. A method of forming a heterogeneous modular engineered tissue construct, the method comprising;

providing a plurality of ring-shaped, self-assembled, scaffold-free, high-density cell aggregates, at least one cell aggregate including a plurality of cells and a plurality of biocompatible and biodegradable nanoparticles and/or microparticles that are incorporated within the cell aggregates, wherein at least one of the plurality of ring-shaped, self-assembled, scaffold-free, high-density cell aggregates is formed by:
　culturing a suspension of nanoparticles and/or microparticles and undifferentiated and/or substantially differentiated progenitor cells in an annular well to form a ring-shaped, self-assembled, scaffold-free, high-density cell aggregate; and
　removing the ring-shaped, self-assembled, scaffold-free, high-density cell aggregate;
the nanoparticles and/or microparticles acting as a bulking agent within the cell aggregate to increase the cell aggregate size and/or thickness and improve the mechanical properties of the cell aggregate; and
the nanoparticles and/or microparticles including at least one bioactive agent for delivery of the at least one bioactive agent, wherein the at least one bioactive agent is differentially and/or controllably released by the nanoparticles and/or microparticles;
stacking the plurality of ring-shaped, self-assembled, scaffold-free, high-density cell aggregates on a support; and
culturing the stacked ring-shaped, self-assembled, scaffold-free, high-density cell aggregates on the solid support in a culture medium to fuse the aggregates and promote tissue formation, wherein the stacked, ring-shaped, self-assembled, scaffold-free, high-density cell aggregates include alternating first engineered ring-shaped, self-assembled, scaffold-free, high-density cell aggregates and second engineered ring-shaped, self-assembled, scaffold-free, high-density cell aggregates, wherein the first and second engineered stacked ring-shaped, self-assembled, scaffold-free, high-density cell aggregates form a heterogeneous tubular shaped construct;
wherein the plurality of ring-shaped, self-assembled, scaffold-free, high-density cell aggregates comprise differing aggregate materials, at least one of the ring-shaped self-assembled, scaffold-free, high-density cell aggregates being provided or formed with or without nanoparticles and/or microparticles and having different properties than the other aggregates to vary the properties of the construct for particular tissue engineering application.

* * * * *